United States Patent
Cheng

(10) Patent No.: US 9,322,002 B2
(45) Date of Patent: *Apr. 26, 2016

(54) SSO7-POLYMERASE CONJUGATES WITH DECREASED NON-SPECIFIC ACTIVITY

(71) Applicant: Bio-Rad Laboratories, Inc., Hercules, CA (US)

(72) Inventor: Man Cheng, Danville, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 29 days.

This patent is subject to a terminal disclaimer.

(21) Appl. No.: 14/186,030

(22) Filed: Feb. 21, 2014

(65) Prior Publication Data

US 2014/0170729 A1 Jun. 19, 2014

Related U.S. Application Data

(62) Division of application No. 13/371,126, filed on Feb. 10, 2012, now Pat. No. 8,697,410.

(60) Provisional application No. 61/499,873, filed on Jun. 22, 2011, provisional application No. 61/473,682, filed on Apr. 8, 2011.

(51) Int. Cl.
*C12N 9/12* (2006.01)
*C12N 9/96* (2006.01)
*C12Q 1/68* (2006.01)

(52) U.S. Cl.
CPC ............ *C12N 9/1241* (2013.01); *C12N 9/1252* (2013.01); *C12N 9/96* (2013.01); *C07K 2319/80* (2013.01); *C12Q 1/686* (2013.01)

(58) Field of Classification Search
None
See application file for complete search history.

(56) References Cited

U.S. PATENT DOCUMENTS

| 4,246,194 | A | 1/1981 | Ferguson |
| 5,565,427 | A | 10/1996 | Freudenberg |
| 6,063,566 | A | 5/2000 | Joyce |
| 6,413,747 | B1 | 7/2002 | Kato et al. |
| 7,560,260 | B2 | 7/2009 | Vander Horn et al. |
| 7,666,645 | B2 | 2/2010 | Wang et al. |
| 7,704,712 | B2 | 4/2010 | Borns |
| 7,838,233 | B2 | 11/2010 | Korfhage et al. |
| 2003/0073081 | A1 | 4/2003 | Mukai et al. |
| 2004/0002076 | A1 | 1/2004 | Wang et al. |
| 2005/0069908 | A1 | 3/2005 | Sorge et al. |
| 2005/0277121 | A1 | 12/2005 | Pasloske et al. |
| 2009/0137008 | A1 | 5/2009 | Gong et al. |
| 2010/0035238 | A1 | 2/2010 | Westberry |
| 2010/0209912 | A1 | 8/2010 | Korfhage et al. |
| 2012/0142070 | A1 | 6/2012 | Battrell et al. |

FOREIGN PATENT DOCUMENTS

| WO | 00/48635 A2 | 8/2000 |
| WO | 2004/011605 A2 | 2/2004 |
| WO | 2004/037979 A1 | 6/2004 |
| WO | 2005/076908 A2 | 8/2005 |
| WO | 2010/080910 A1 | 7/2010 |

OTHER PUBLICATIONS

Wang et al. (Nucleic Acids Research, vol. 32, pp. 1197-1207, 2004.*
Ngo et al. in the Protein Folding Problem and Tertiary Structure Prediction, 1994, Merz et al. (ed.), Birkhauser, Boston, MA, pp. 433 and 492-495.*
Choli et al.; "Isolation, characterization and microsequence analysis of a small basic methylated DNA-binding protein from the Archaebacterium, *Sulfolobus solfataricus*"; *Biochimica et Biophysica Acta.* 950:193-203 (1988).
Extended European Search Report from Appl. No. EP 12768058.5, dated Nov. 19, 2014.
Gao et al.; "The crystal structure of the hyperthermophile chromosomal protein Sso7d bound to DNA"; *Nat. Struct. Biol.*; 5(9):782-786 (1998).
"SsoFast™ EvaGreen® Supermix"; Flier, Rev.B. Bio-Rad Laboratories, Inc. Sep. 8, 2010 (2 pages) Retrieved from the internet at bio-rad.com/webroot/web/pdflsr/literature/Bulletin_5816.pdf.
Ashton et al.; "The effect of temperature of pH measurement"; Reagecon Diagnostis Ltd., Technical Paper; Oct. 17, 2006 (7 pages).
Baumann et al.; "DNA-binding surface of the Sso7d protein from *Sulfolous solfataricus*"; *J. Mol. Biol.*; 247:840-846 (1995).
Wan et al.; "Spermidine facilitates PCR amplification of target DNA"; PCR Methods and Applications; 3(3):208-210 (1993).
Notice of Allowability from U.S. Appl. No. 13/371,126, dated Nov. 14, 2013.
Office Action from U.S. Appl. No. 13/370,604, dated Dec. 19, 2013.
International Search Report and Written Opinion from PCT/US2012/024735, dated Jul. 12, 2012 (13 pages).
International Search Report and Written Opinion from PCT/US2012/024739, dated Jul. 12, 2012 (11 pages).
U.S. Appl. No. 13/165,373, filed Jun. 21, 2011 (137 pages).

* cited by examiner

*Primary Examiner* — Richard Hutson
(74) *Attorney, Agent, or Firm* — Kilpatrick Townsend and Stockton LLP

(57) ABSTRACT

Improved Sso7-polymerase conjugate proteins are provided.

20 Claims, 1 Drawing Sheet

Alignment result of Sso7d variants

CLUSTAL 2.1 multiple sequence alignment

```
Sso7d/Ssh7A/SsoP2    MATVKFKYKGEEKEVDISKIKKVWRVGKMISFTYDEGGGKTGRGAVSEKDAPKELLQMLE  60
Ssh7b                MVTVKFKYKGEEKEVDTSKIKKVWRVGKMISFTYDEGGGKTGRGAVSEKDAPKELLQMLE  60
Sto7e                MVTVKFKYKGEEKEVDISKIKKVWRVGKMISFTYDDNG-KTGRGAVSEKDAPKELLQMLE  59
Sac7d                MVKVKFKYKGEEKEVDTSKIKKVWRVGKMVSFTYDDNG-KTGRGAVSEKDAPKELLDMLA  59
Sac7e                MAKVRFKYKGEEKEVDTSKIKKVWRVGKMVSFTYDDNG-KTGRGAVSEKDAPKELMDMLA  59
                     *..*:.***********:********** ******::.* ******************::.**

Sso7d/Ssh7A/SsoP2    KQ-KK--  64
Ssh7b                KQ-KK--  64
Sto7e                KSGKK--  64
Sac7d                RAEREKK  66
Sac7e                RAEKKK-  65
                     :  ::
```

Bolded and underlined K = K28

Bolded and underlined R = R43

SSO7-POLYMERASE CONJUGATES WITH DECREASED NON-SPECIFIC ACTIVITY

CROSS-REFERENCE TO RELATED PATENT APPLICATIONS

The present application is a divisional of U.S. patent application Ser. No. 13/371,126, filed Feb. 10, 2012, which claims benefit of priority to U.S. Provisional Patent Application No. 61/473,682, filed Apr. 8, 2011, and to U.S. Provisional Patent Application No. 61/499,873, filed Jun. 22, 2011, each of which are incorporated by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file SEQTXT_94260-900708, created on Feb. 20, 2014, 225,173 bytes, machine format IBM-PC, MS-Windows operating system, is hereby incorporated by reference in its entirety for all purposes.

BACKGROUND OF THE INVENTION

Nucleic acid amplification reactions, such as the polymerase chain reaction (PCR), are generally template-dependent reactions in which a desired nucleic acid sequence is amplified by treating separate complementary strands of a target nucleic acid with an excess of two oligonucleotide primers. The primers are extended to form complementary primer extension products which act as templates for synthesizing the desired nucleic acid sequence. In such processes, the nucleic acid sequence between the primers on the respective DNA strands is selectively amplified.

The activity of a polymerase can be improved by joining a sequence-non-specific double-stranded nucleic acid binding domain to the enzyme, or its catalytic domain (see, e.g., WO0192501). Such modified polymerases exhibit increased processivity in comparison to the unmodified enzymes.

BRIEF SUMMARY OF THE INVENTION

The present invention provides for an Sso7 polymerase conjugate protein comprising an Sso7 domain linked to a polymerase; wherein:
an amino acid of the Sso7 domain corresponding to K28 of SEQ ID NO:2 is not lysine (K); and/or
an amino acid of the Sso7 domain corresponding to R43 of SEQ ID NO:2 is not arginine (R),
wherein the conjugate protein has a decreased non-specific amplification activity compared to an otherwise identical control conjugate protein in which the amino acid of the Sso7 domain corresponding to K28 of SEQ ID NO:2 is lysine (K) and the amino acid of the Sso7 domain corresponding to R43 of SEQ ID NO:2 is arginine (R).

In some embodiments, the non-specific amplification activity of the Sso7 polymerase conjugate protein is reduced by at least 10% compared to non-specific amplification activity of the control conjugate protein.

In some embodiments, the amino acid of the Sso7 domain corresponding to K28 of SEQ ID NO:2 is not lysine (K). In some embodiments, the amino acid of the Sso7 domain corresponding to K28 of SEQ ID NO:2 is selected from the group consisting of serine (S), threonine (T), cysteine (C), proline (P), aspartic acid (D), glutamic acid (E), asparagine (N), glutamine (Q), alanine (A), phenylalanine (F), glycine (G), histidine (H), isoleucine (I), leucine (L), methionine (M), arginine (R), valine (V), tryptophan (W), and tyrosine (Y).

In some embodiments, the amino acid of the Sso7 domain corresponding to R43 of SEQ ID NO:2 is not arginine (R). In some embodiments, the amino acid of the Sso7 domain corresponding to R43 of SEQ ID NO:2 is selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), glutamine (Q), serine (S), threonine (T), valine (V), tryptophan (W), tyrosine (Y), and proline (P).

In some embodiments, the polymerase substantially lacks a 3'-5' exonuclease activity.

In some embodiments, the Sso7 domain is substantially (e.g., at least 60, 75, 80, 85, 90, or 95%) identical to the first 58 or 60 amino acids of SEQ ID NO:2 or to the full-length of SEQ ID NO:2. In some embodiments, the Sso7 domain is at least 90% identical to SEQ ID NO:2.

In some embodiments, the polymerase is substantially (e.g., at least 60, 75, 80, 85, 90, or 95%) identical to SEQ ID NO:33 or SEQ ID NO:34 or SEQ ID NO:61. In some embodiments, the polymerase comprises SEQ ID NO:33 or SEQ ID NO:34 or SEQ ID NO:61.

In some embodiments, the polymerase domain has thermally stable polymerase activity. In some embodiments, the polymerase domain is a family A polymerase domain. In some embodiments, the polymerase domain is a ΔTaq polymerase domain.

In some embodiments, the polymerase domain is a family B polymerase domain. In some embodiments, the polymerase domain is from *Pyrococcus*.

The present invention also provides for reaction mixtures comprising a Sso7 polymerase conjugate proteins as described above or elsewhere herein. In some embodiments, the kit further comprises at least one of or more oligonucleotide primers, one or more detectably-labeled oligonucleotide probe, a buffer, nucleoside triphosphates (dNTPs), a salt, a DNA binding dye, or a stabilizer.

The present invention also provides for kits that comprise Sso7 polymerase conjugate proteins as described above or elsewhere herein. In some embodiments, the kit further comprises, in the same or a different container that contains the conjugate protein, at least one of one or more oligonucleotide primers, one or more detectably-labeled oligonucleotide probe, a buffer, nucleoside triphosphates (dNTPs), a salt, or a stabilizer.

In some embodiments, the composition comprises a buffer (when measured at a concentration of 0.1 M) that has a change of no more than 0.027 pH units per degree C. when between 20° and 37° C. In some embodiments, the buffer is selected from the group consisting of HEPES, ACES, PIPES, MOPSO, BES, MOPS, TES, TAPSO, POPSO, BICINE, TAPS, and AMPSO.

The present invention also provides for methods of amplifying a target nucleic acid in a sample. In some embodiments the method comprises incubating the target nucleic acid in a reaction mixture comprising:
a. at least one primer; and
b. a Sso7 polymerase conjugate proteins as described above or elsewhere herein, under conditions to allow for amplification of the target nucleic acid with the primer, thereby amplifying the target nucleic acid.

In some embodiments, the method comprises a polymerase chain reaction (PCR).

The present invention also provides for nucleic acids comprising a polynucleotide encoding a Sso7 polymerase conjugate proteins as described above or elsewhere herein. In some embodiments, the amino acid of the Sso7 domain corresponding to K28 of SEQ ID NO:2 is not lysine (K). In some embodiments, the amino acid of the Sso7 domain corresponding to K28 of SEQ ID NO:2 is selected from the group consisting of serine (S), threonine (T), cysteine (C), proline (P), aspartic acid (D), glutamic acid (E), asparagine (N), glutamine (Q), alanine (A), phenylalanine (F), glycine (G), histidine (H), isoleucine (I), leucine (L), methionine (M), arginine (R), valine (V), tryptophan (W), and tyrosine (Y).

In some embodiments, the amino acid of the Sso7 domain corresponding to R43 of SEQ ID NO:2 is not arginine (R). In some embodiments, the amino acid of the Sso7 domain corresponding to R43 of SEQ ID NO:2 is selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), glutamine (Q), serine (S), threonine (T), valine (V), tryptophan (W), tyrosine (Y), and proline (P).

In some embodiments, the polymerase substantially lacks a 3'-5' exonuclease activity.

In some embodiments, the Sso7 domain is substantially (e.g., at least 60, 75, 80, 85, 90, or 95%) identical to the first 58 or 60 amino acids of SEQ ID NO:2 or to the full-length of SEQ ID NO:2. In some embodiments, the Sso7 domain is at least 90% identical to SEQ ID NO:2.

In some embodiments, the polymerase is substantially (e.g., at least 60, 75, 80, 85, 90, or 95%) identical to SEQ ID NO:33 or SEQ ID NO:34 or SEQ ID NO:61. In some embodiments, the polymerase comprises SEQ ID NO:33 or SEQ ID NO:34 or SEQ ID NO:61.

The present invention also provides for a cell comprising a recombinant expression cassette, the expression cassette comprising a promoter operably linked to a polynucleotide encoding a Sso7 polymerase conjugate proteins as described above or elsewhere herein. In some embodiments, the amino acid of the Sso7 domain corresponding to K28 of SEQ ID NO:2 is not lysine (K). In some embodiments, the amino acid of the Sso7 domain corresponding to K28 of SEQ ID NO:2 is selected from the group consisting of serine (S), threonine (T), cysteine (C), proline (P), aspartic acid (D), glutamic acid (E), asparagine (N), glutamine (Q), alanine (A), phenylalanine (F), glycine (G), histidine (H), isoleucine (I), leucine (L), methionine (M), arginine (R), valine (V), tryptophan (W), and tyrosine (Y).

In some embodiments, the amino acid of the Sso7 domain corresponding to R43 of SEQ ID NO:2 is not arginine (R). In some embodiments, the amino acid of the Sso7 domain corresponding to R43 of SEQ ID NO:2 is selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), glutamine (Q), serine (S), threonine (T), valine (V), tryptophan (W), tyrosine (Y), and proline (P).

In some embodiments, the polymerase substantially lacks a 3'-5' exonuclease activity.

In some embodiments, the Sso7 domain is substantially (e.g., at least 60, 75, 80, 85, 90, or 95%) identical to the first 58 or 60 amino acids of SEQ ID NO:2 or to the full-length of SEQ ID NO:2. In some embodiments, the Sso7 domain is at least 90% identical to SEQ ID NO:2.

In some embodiments, the polymerase is substantially (e.g., at least 60, 75, 80, 85, 90, or 95%) identical to SEQ ID NO:33 or SEQ ID NO:34 or SEQ ID NO:61. In some embodiments, the polymerase comprises SEQ ID NO:33 or SEQ ID NO:34 or SEQ ID NO:61.

BRIEF DESCRIPTION OF THE DRAWINGS

FIG. 1. Alignment of various Sso7 amino acid sequences (SEQ ID NOS:2, 3, 6, 4 and 5, respectively).

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art.

The term "Sso7" or "Sso7 DNA binding domain" or "Sso7-like DNA binding domain" or "Sso7 domain" refers to nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity to SEQ ID NO:2; (2) specifically hybridize under stringent hybridization conditions to a Sso7d nucleic acid sequence of SEQ ID NO:1 and conservatively modified variants thereof; or (3) have a nucleic acid sequence that has greater than about 90%, 91%, 92%, 93%, 94%, 95%, 96%, 97%, 98%, 99%, or higher nucleotide sequence identity to SEQ ID NO:1. The term includes both full-length Sso7d polypeptides and fragments of the polypeptides that have sequence non-specific double-stranded binding activity. Sso7-like proteins include, but are not limited to, Sso7d, Sac7d and Sac7e.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

"Heterologous", when used with reference to portions of a protein, indicates that the protein comprises two or more domains that are not found in the same relationship to each other in nature. Such a protein, e.g., a fusion protein, contains two or more domains from unrelated proteins arranged to make a new functional protein.

"Join" refers to any method known in the art for functionally connecting protein domains, including without limitation recombinant fusion with or without intervening domains, intein-mediated fusion, non-covalent association, and covalent bonding, including disulfide bonding; hydrogen bonding; electrostatic bonding; and conformational bonding, e.g., antibody-antigen, and biotin-avidin associations.

"Thermally stable polymerase" as used herein refers to any enzyme that catalyzes polynucleotide synthesis by addition of nucleotide units to a nucleotide chain using DNA or RNA as a template and has an optimal activity at a temperature above 45° C.

"*Thermus* polymerase" refers to a family A DNA polymerase isolated from any *Thermus* species, including without limitation *Thermus aquaticus, Thermus brockianus*, and *Thermus thermophilus*; any recombinant polymerases deriving from *Thermus* species, and any functional derivatives thereof, whether derived by genetic modification or chemical modification or other methods known in the art.

The term "amplification reaction" refers to any in vitro means for multiplying the copies of a target sequence of nucleic acid. Such methods include but are not limited to polymerase chain reaction (PCR), DNA ligase chain reaction (see U.S. Pat. Nos. 4,683,195 and 4,683,202; PCR Protocols: A Guide to Methods and Applications (Innis et al., eds, 1990)), (LCR), QBeta RNA replicase, and RNA transcription-based (such as TAS and 3SR) amplification reactions as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. As discussed further herein, amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

The term "specificity," as used with respect to nucleic acid amplification, refers to the likelihood of a nucleic acid amplification reaction producing specific amplification products as compared to non-specific amplification products. A "specific amplification product" refers to the polynucleotide produced by amplification with correctly matched primers and template (i.e., the true target sequence). A "non-specific amplification product" refers to the polynucleotide produced by amplification with mismatched primers and template.

The phrase "improve specificity" or "improving specificity," as used with respect to nucleic acid amplification, refers to a detectable increase in the amount of specific amplification products produced in a nucleic acid amplification as compared to the amount of non-specific amplification products produced. Specificity of an amplification reaction can be measured according to any method, including but not limited to melt-curve analysis or gel analysis. In some embodiments, the specificity of a nucleic acid amplification reaction is determined by comparing the relative yield of two products, one of which is the specific product with the expected $T_m$ and the other the non-specific product with a lower or higher $T_m$ than that of the specific product. A reaction mixture comprising an Sso7-polymerase conjugate having an Sso7 domain with a K28 and/or R43 mutation as described herein will have a higher relative yield in an amplification reaction of the specific product than the non-specific product (i.e., the ratio of the yield as measured by the height of the melting peak of the specific product over the height of the melting peak of the non-specific product) than the relative yield of the specific product over the non-specific product in a reaction mixture having a control polymerase with the wildtype Sso7 domain. In some embodiments, an Sso7-polymerase conjugate having an Sso7 domain with a K28 and/or R43 mutation as described herein will have improved amplification specificity of at least 10%, 15%, 20%, 25%, 30%, 40%, 50%, 100%, 2-fold (200%), 2.5-fold (250%), 3-fold (300%) or greater increase in the ratio relative to reactions in which a control polymerase having the wildtype Sso7 domain.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra.

A "template" refers to a polynucleotide sequence that comprises the polynucleotide to be amplified, flanked by primer hybridization sites. Thus, a "target template" comprises the target polynucleotide sequence flanked by hybridization sites for a 5' primer and a 3' primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine.

Amino acid analogs refers to compounds that have the same basic chemical structure as a naturally occurring amino acid, i.e., a carbon atom that is bound to a hydrogen atom, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The term "encoding" refers to a polynucleotide sequence encoding one or more amino acids. The term does not require a start or stop codon. An amino acid sequence can be encoded in any one of six different reading frames provided by a polynucleotide sequence.

The term "promoter" refers to regions or sequence located upstream and/or downstream from the start of transcription and which are involved in recognition and binding of RNA polymerase and other proteins to initiate transcription.

A "vector" refers to a polynucleotide, which when independent of the host chromosome, is capable replication in a host organism. Preferred vectors include plasmids and typically have an origin of replication. Vectors can comprise, e.g., transcription and translation terminators, transcription and translation initiation sequences, and promoters useful for regulation of the expression of the particular nucleic acid.

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., Molecular Cloning—A Laboratory Manual, Cold Spring Harbor Laboratory, Cold Spring Harbor, N.Y., (1989) or Current Protocols in Molecular Biology Volumes 1-3, John Wiley & Sons, Inc. (1994-1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis*, and *Thermotoga maritime*, or modified versions there of. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases $\alpha$, $\lambda$, and $\epsilon$, are implicated in nuclear replication, and a family A polymerase, polymerase $\gamma$, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

Sequences are "substantially identical" to each other if they have a specified percentage of nucleotides or amino acid residues that are the same (e.g., at least 60%, 65%, 70%, 75%, 80%, 85%, 90%, 91%, 92%, 93%, 94%, 95%, 96%, 97%, 98%, or 99% identity over a specified region), when compared and aligned for maximum correspondence over a comparison window, or designated region as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Accelrys), or by manual alignment and visual inspection.

Algorithms suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, highly stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Hybridization conditions are typically those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions.

Exemplary "moderately stringent hybridization conditions" include a hybridization in a buffer of 40% formamide, 1 M NaCl, 1% SDS at 37° C., and a wash in 1× SSC at 45° C. Exemplary "stringent hybridization conditions" include a hybridization in a buffer of 40% formamide, 1 M NaCl, 1% SDS at 37° C., and at least one wash in 0.2× SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

DETAILED DESCRIPTION OF THE INVENTION

I. Introduction

The current invention provides variant Sso7 polymerase conjugates that exhibit reduced non-specific amplification activity compared to Sso7 polymerase conjugates comprising wildtype Sso7 domains. The variant Sso7 polymerase conjugates comprise at least a polymerase domain joined to a variant Sso7 binding domain. The variant Sso7 DNA-binding domains comprise an amino acid change at one or both of two positions (corresponding to K28 and/or R43 in SEQ ID NO:2) as compared to the wildtype amino acid at that position. As demonstrated in the Examples, a number of different amino acid substitutions from wildtype at these positions have been shown to reduce non-specific polymerase activity. Non-specific polymerase activity includes amplification of a nucleic acid that occur other than due to template-specific extension of a hybridized primer.

II. Sso7 Domains of the Invention

The polymerase conjugates of the invention comprise an Sso7 polypeptide sequence that has amino acid substitutions compared to the native (wildtype) Sso7d sequence. Sso7d is a small (63 amino acids, about 7 kd MW), basic chromosomal protein from the hyperthermophilic archaeabacteria *Sulfolobus solfataricus*. The protein is lysine-rich and has high thermal, acid and chemical stability. It binds to DNA in a sequence-independent manner and when bound, increase the Tm of DNA by up to 40° C. under some conditions (McAfee et al., Biochemistry 34:10063-10077, 1995). Sso7d and its homologs are typically believed to be involved in packaging genomic DNA and stabilizing genomic DNA at elevated temperatures. The Sso7d protein sequence is set forth in SEQ ID NO:2.

There are several known Sso7d-like proteins (also referred to as "Sso7 proteins") including, but not limited to, Sac7a, Sac7b, Sac7d (SEQ ID NO:4), Sac7e (SEQ ID NO:5), from the hyperthermophilic archaeabacteria *Sulfolobus acidocaldarius*; Sto7e (SEQ ID NO:6) from *Sulfolobus tokodaii*, and Ssh7a and Ssh7b (SEQ ID NO:3) from *Sulfolobus shibatae* (see, e.g., UniProt database accession numbers: P39476 (Sso7d); O59632 (Ssh7b); P13123 (Sac7d); P13125 (Sac7e); and Q96X56 (Sto7e)). These proteins have an identity with Sso7d that ranges from 78% to 98%. Other Sso7 domains for use in the invention may also be identified as set forth below.

As noted herein, the invention provides for amino acid changes from the native amino acid at the positions corresponding to K28 and/or R43 of SEQ ID NO:2. It should be understood that such position designations do not indicate the number of amino acids in the claimed molecule per se, but indicate where in the claimed molecule the residue occurs when the claimed molecule sequence is maximally aligned with SEQ ID NO:2. In the context of variant Sso7 domains, "correspondence" to a Sso7-like protein sequence is based on the convention of numbering according to amino acid position number of a particular sequence (i.e., SEQ ID NO:2) and then aligning the Sso7-like protein sequence in a manner that maximizes the percentage of sequence identity to SEQ ID NO:2. Alignment can be performed either manually or using a sequence comparison algorithm (e.g., using the NCBI BLAST program with default parameters (see, e.g., Altschul et al., *Nucl. Acids Res.* 25:3389-3402, 1997). An example of an alignment of several Sso7-like proteins with SEQ ID NO:2 is shown in FIG. 1. The corresponding sequences can be summarized as follows:

| | Actual position of amino acid corresponding to K28 of SEQ ID NO: 2 | Actual position of amino acid corresponding to R43 of SEQ ID NO: 2 |
|---|---|---|
| Sso7 (SEQ ID NO: 2) | 28 | 43 |
| Ssh7b (SEQ ID NO: 3) | 28 | 43 |
| Sto7e (SEQ ID NO: 4) | 28 | 42 |
| Sac7d (SEQ ID NO: 5) | 28 | 42 |
| Sac7e (SEQ ID NO: 6) | 28 | 42 |

Any Sso7 DNA binding protein domain can be substituted at the K28 and/or R43 position corresponding to SEQ ID NO:2. Thus, for example, in some embodiments, the variant Sso7 polypeptide sequence is substantially (e.g., at least 60, 70, 80, 85, 90, or 95%) identical to any of, e.g., SEQ ID NOS:2, 3, 4, 5, or 6, and comprises an amino acid other than K at the amino acid position corresponding to K28. In some embodiments, the amino acid position corresponding to K28 is serine (S), threonine (T), cysteine (C), proline (P), aspartic acid (D), glutamic acid (E), asparagine (N), glutamine (Q), alanine (A), phenylalanine (F), glycine (G), histidine (H), isoleucine (I), leucine (L), methionine (M), arginine (R), valine (V), tryptophan (W), or tyrosine (Y).

In some embodiments, the variant Sso7 polypeptide sequence is substantially (e.g., at least 60, 70, 80, 85, 90, or 95%) identical to any of, e.g., SEQ ID NOS:2, 3, 4, 5, or 6, and comprises an amino acid other than R at the amino acid position corresponding to R43. In some embodiments, the amino acid position corresponding to R43 is alanine (A), cysteine (C), aspartic acid (D), glutamic acid (E), phenylalanine (F), glycine (G), histidine (H), isoleucine (I), lysine (K), leucine (L), methionine (M), asparagine (N), glutamine (Q), serine (S), threonine (T), valine (V), tryptophan (W), tyrosine (Y), or proline (P).

In some embodiments, the variant Sso7 polypeptide sequence is substantially (e.g., at least 60, 70, 80, 85, 90, or 95%) identical to any of, e.g., SEQ ID NOS:2, 3, 4, 5, or 6, and comprises an amino acid other than K at the amino acid position corresponding to K28 and an amino acid other than R at the amino acid position corresponding to R43. For example, in some embodiments, the amino acid at position K28 is selected from: serine (S), threonine (T), cysteine (C), proline (P), aspartic acid (D), glutamic acid (E), asparagine (N), glutamine (Q), alanine (A), phenylalanine (F), glycine (G), histidine (H), isoleucine (I), leucine (L), valine (V), tryptophan (W), or tyrosine (Y) and the amino acid at position R43 is selected from: alanine (A), cysteine (C), aspartic acid (D), glutamic acid (E), phenylalanine (F), glycine (G), histidine (H), isoleucine (I), lysine (K), leucine (L), methionine (M), asparagine (N), glutamine (Q), serine (S), threonine (T), valine (V), tryptophan (W), tyrosine (Y), or proline (P).

There are many ways of generating these alterations or variants of a given nucleic acid sequence. Well-known methods include, e.g., site-directed mutagenesis, PCR amplification using degenerate oligonucleotides, chemical synthesis of a desired oligonucleotide (e.g., in conjunction with ligation and/or cloning to generate large nucleic acids) and other well-known techniques. See, Giliman & Smith, Gene 8:81-97 (1979), Roberts, et al., Nature 328:731-734 (1987) and Sambrook, Innis, and Ausubel (all supra).

In some embodiments, the variant Sso7 domain or polypeptide sequence is identical or substantially identical (e.g., has at least 60%, 65%, 70%, 75%, 80%, 85%, 90%, 91%, 92%, 93%, 94%, 95%, 96%, 97%, 98%, or 99% amino acid sequence identity) to an amino acid sequence of any of SEQ ID NOS:7-32. In some embodiments, the Sso7 domain or protein has the amino acid sequence of any of SEQ ID NOS:7-32.

In one example of generating an Sso7 sequence of the invention, site directed mutagenesis is used to substitute an amino acid residue. The nucleic acid sequence is substituting by synthesizing an oligonucleotide primer that contains the mutation. In some embodiments, the primer is hybridized to an Sso7 nucleic acid, e.g., SEQ ID NO:1, and a new sequence amplified. The amplification product with the mutation may then ligated into an expression vector.

In some embodiments, polypeptide sequences are altered as above, i.e., by changing the corresponding nucleic acid sequence and expressing the polypeptide. However, polypeptide sequences can also be generated synthetically using commercially available peptide synthesizers to produce a desired polypeptide (see, Merrifield, and Stewart & Young, supra).

Finally, the substituted Sso7 sequences are evaluated by using techniques such as those described herein to identify the fusion polymerases that exhibit reduced non-specific polymerase activity.

III. Polymerases

In general it is believed that essentially any polymerase can be linked to a variant Sso7 protein sequence of the invention to form the Sso7-polymerase conjugate protein of the invention, thereby improving various activities of the polymerase. In one exemplary embodiment, the Sso7 polymerase conjugate protein comprises a polymerase domain derived from two parental polymerases, Pfu and DeepVent. Such polymerases are described for example in U.S. Application Publication Nos. 20040219558; 20040214194; 20040191825; 20030162173, each of which is hereby incorporated by reference in its entirety for all purposes and in particular for all teachings related to hybrid polymerases. In some embodiments, the polymerase is substantially (e.g., at least 60, 70, 80, 85, 90, or 95%) identical to SEQ ID NO:33 or SEQ ID NO:34 or SEQ ID NO:61.

A variety of polymerases can be used as at least a portion of the polymerase domain of polymerase. At least five families of DNA-dependent DNA polymerases are known, although most fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, λ, and ε are implicated in nuclear replication, and a family A polymerase, polymerase γ, is used for mitochondrial DNA replication. Other types of DNA polymerases include phage polymerases. Any of these polymerases, combinations of all or portions of these polymerases, as well as chimeras or hybrids between two or more of such polymerases or their equivalents can be used to form a portion or all of the polymerase domain of Sso7 polymerase conjugate proteins of the invention.

In one exemplary embodiment, the polymerase conjugates of the invention have a polymerase domain derived from two parental polymerases, Pfu and DeepVent. Such polymerases are described for example in U.S. Application Publication Nos. 20040219558; 20040214194; 20040191825; 20030162173, each of which is hereby incorporated by reference in its entirety for all purposes and in particular for all teachings related to hybrid polymerases. In some embodiments, the polymerase is substantially (e.g., at least 60, 70, 80, 85, 90, or 95%) identical to SEQ ID NO:34 (optionally including a linker such as SEQ ID NO:62) or SEQ ID NO:33 (optionally including a linker such as SEQ ID NO:62) or SEQ ID NO:61.

Further, in some embodiments, non-thermostable polymerases may also be used in accordance with the invention. For example, the large fragment of *E. coli* DNA Polymerase I (Klenow) (the Klenow Fragment) with mutation (D355A, E357A) abolishes the 3'→5' exonuclease activity. This enzyme or equivalent enzymes can be used, for example, in embodiments where the amplification reaction is not performed at high temperatures.

In some embodiments, the hybrid polymerases of the invention include a polymerase domain comprising mutations that reduce or abolish exonuclease activity of any hybrid polymerase comprising such a polymerase domain in comparison to a Sso7 polymerase conjugate protein comprising a polymerase domain that does not have such mutations. A variety of mutations can be introduced into a native polymerase domain to reduce or eliminate 3'-5' exonuclease activity. For example, U.S. Pat. Nos. 6,015,668; 5,939,301 and 5,948,614 describe mutations of a metal-binding aspartate to an alanine residue in the 3'-5' exonuclease domain of the Tma and Tne DNA polymerases. These mutations reduce the 3'-5' exonuclease activities of these enzymes to below detectable levels. Similarly, U.S. Pat. No. 5,882,904 describes an analogous aspartate-to-alanine mutation in *Thermococcus barossi*, and U.S. Pat. No. 5,489,523 teaches the double-mutant D141A E143A of the *Pyrococcus wosei* DNA polymerases. Both of these mutant polymerases have virtually no detectable 3'-5' exonuclease activity. Methods of assaying 3'-5' exonuclease activity are well-known in the art. See, e.g., Freemont et al., *Proteins* 1:66 (1986); Derbyshire et al., *EMBO J.* 16:17 (1991) and Derbyshire et al., *Methods in Enzymology* 262:363 85 (1995). It will be understood that while the above-described mutations were originally identified in one polymerase, one can generally introduce such mutations into other polymerases to reduce or eliminate exonuclease activity. In a specific embodiment, a polymerases of the invention comprise the double point mutation D141A/E143A in the polymerase domain. The phrase "corresponding to a position," in reference to polymerase amino acids, refers to an amino acid that aligns with the same amino acid (e.g., D141 or E143) in a reference polymerase amino acid sequence (e.g., SEQ ID NO:2, optionally including a linker such as SEQ ID NO:62). Sequence comparisons can be performed using any BLAST including BLAST 2.2 algorithm with default parameters, described in Altschul et al., *Nuc.*

*Acids Res.* 25:3389 3402 (1977) and Altschul et al., *J. Mol. Biol.* 215:403 410 (1990), respectively. Thus, in some embodiments, Sso7 polymerase conjugate proteins comprise mutations in the exonuclease domain. For example, in some embodiments, the Sso7d polymerase conjugate is substantially (e.g., at least 80%, 85%, 90%, 95%, 98% or 100%) identical to SEQ ID NO:61, comprises one or more mutation reducing exonuclease activity while substantially retaining polymerase activity, and is conjugated to an Sso7d DNA binding domain as described herein. In still further embodiments, such Sso7 polymerase conjugate proteins comprise an amino acid sequence according to SEQ ID NO:33 (optionally including a linker such as SEQ ID NO:62).

IV. Conjugates

The Sso7 DNA binding domain and the polymerase can be joined to form a Sso7-polymerase conjugate by methods well known to those of skill in the art. These methods include both chemical and recombinant means.

Chemical joining the Sso7 protein to the polymerase can be performed, for example as described in Bioconjugate Techniques, Hermanson, Ed., Academic Press (1996). Joining can include, for example, derivitization for the purpose of linking the two proteins to each other, either directly or through a linking compound, by methods that are well known in the art of protein chemistry. For example, in one chemical conjugation embodiment, the means of linking the catalytic domain and the nucleic acid binding domain comprises a heterobifunctional-coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteines in each moiety, which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages.

The means of linking the Sso7 and polymerase domains of the conjugate protein may also comprise a peptidyl bond formed between moieties that are separately synthesized by standard peptide synthesis chemistry or recombinant means. The conjugate protein itself can also be produced using chemical methods to synthesize an amino acid sequence in whole or in part. For example, peptides can be synthesized by solid phase techniques, such as, e.g., the Merrifield solid phase synthesis method, in which amino acids are sequentially added to a growing chain of amino acids (see, Merrifield (1963) J. Am. Chem. Soc., 85:2149-2146). Equipment for automated synthesis of polypeptides is commercially available from suppliers such as PE Corp. (Foster City, Calif.), and may generally be operated according to the manufacturer's instructions. The synthesized peptides can then be cleaved from the resin, and purified, e.g., by preparative high performance liquid chromatography (see Creighton, Proteins Structures and Molecular Principles, 50-60 (1983)). The composition of the synthetic polypeptides or of subfragments of the polypeptide, may be confirmed by amino acid analysis or sequencing (e.g., the Edman degradation procedure; see Creighton, Proteins, Structures and Molecular Principles, pp. 34-49 (1983)).

In addition, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxy-proline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In another embodiment, the Sso7 and polymerase domains are joined via a linking group. The linking group can be a chemical crosslinking agent, including, for example, succinimidyl-(N-maleimidomethyl)-cyclohexane-1-carboxylate (SMCC). The linking group can also be an additional amino acid sequence(s), including, for example, a polyalanine, polyglycine or similarly, linking group.

Alternatively, in some embodiments, the coding sequences of each polypeptide in the fusion protein are directly joined at their amino- or carboxy-terminus via a peptide bond in any order. Alternatively, an amino acid linker sequence may be employed to separate the first and second polypeptide components by a distance sufficient to ensure that each polypeptide folds into its secondary and tertiary structures. Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Ser, Val and Thr residues. Other near neutral amino acids, such as Ala can also be used in the linker sequence. Amino acid sequences which may be usefully employed as linkers include those disclosed in Maratea et al. (1985) Gene 40:39-46; Murphy et al. (1986) Proc. Natl. Acad. Sci. USA 83:8258-8262; U.S. Pat. Nos. 4,935,233 and 4,751,180. The linker sequence may generally be from 1 to about 50 amino acids in length, e.g., 3, 4, 6, or amino acids in length, but can be 100 or 200 amino acids in length. Linker sequences may not be required when the first and second polypeptides have non-essential N-terminal amino acid regions that can be used to separate the functional domains and prevent steric interference. An exemplary peptide linker is shown in SEQ ID NO:62.

Exemplary conjugates of the invention include those that comprise a polypeptide identical, or substantially (e.g., at least 60, 70, 80, 85, 90, or 95%) identical to any of SEQ ID NOS:35, 36, 37, 38, 39, 40, 41, 42, 43, 44, 45, 46, 47, 48, 49, 50, 51, 52, 53, 54, 55, 56, 57, 58, 59, or 60 so long as the conjugates include the non-native K28 or R43 amino acid in the sequence.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterobifunctional linkages.

Other methods of joining the Sso7 and polymerase domains include ionic binding by expressing negative and positive tails and indirect binding through antibodies and streptavidin-biotin interactions. (See, e.g., Bioconjugate Techniques, supra). The domains may also be joined together through an intermediate interacting sequence. For example, an Sso7d-interacting sequence, i.e., a sequence that binds to Sso7d, can be joined to a polymerase. The resulting fusion protein can then be allowed to associate non-covalently with the Sso7d to generate an Sso7d-polymerase conjugate.

In some embodiments, a conjugate Sso7-polymerase protein of the invention is produced by recombinant expression of a nucleic acid encoding the protein. Such a fusion product can be made by ligating the appropriate nucleic acid sequences encoding the desired amino acid sequences to each other by methods known in the art, in the proper coding frame, and expressing the product by methods known in the art.

Nucleic acids encoding the domains to be incorporated into the fusion proteins of the invention can be obtained using routine techniques in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999).

Nucleic acid sequences that encode the Sso7 and polymerase polypeptides can be obtained using any of a variety of methods. In some embodiments, the nucleic acid sequences encoding the polypeptides are cloned from cDNA and genomic DNA libraries by hybridization with probes, or isolated using amplification techniques with oligonucleotide primers. More commonly, amplification techniques are used to amplify and isolate the Sso7 and polymerase sequences using a DNA or RNA template (see, e.g., Dieffenfach & Dveksler, PCR Primers: A Laboratory Manual (1995)). Alternatively, overlapping oligonucleotides can be produced synthetically and joined to produce one or more of the domains. Nucleic acids encoding catalytic or double-stranded nucleic acid binding domains can also be isolated from expression libraries using antibodies as probes.

In an example of obtaining a nucleic acid encoding an Sso7 or polymerase domain using PCR, the nucleic acid sequence or subsequence is PCR amplified, using a sense primer containing one restriction site and an antisense primer containing another restriction site. This will produce a nucleic acid encoding the desired domain sequence or subsequence and having terminal restriction sites. This nucleic acid can then be ligated into a vector containing a nucleic acid encoding the second domain and having the appropriate corresponding restriction sites. The domains can be directly joined or may be separated by a linker, or other, protein sequence. Suitable PCR primers can be determined by one of skill in the art using the sequence information provided in GenBank or other sources. Appropriate restriction sites can also be added to the nucleic acid encoding the protein or protein subsequence by site-directed mutagenesis. The plasmid containing the domain-encoding nucleotide sequence or subsequence is cleaved with the appropriate restriction endonuclease and then ligated into an appropriate vector for amplification and/or expression according to standard methods.

One of skill will also recognize that modifications can additionally be made to the Sso7 and polymerase domains without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

One or more of the domains may also be modified to facilitate the linkage of the two domains to obtain the polynucleotides that encode the fusion polypeptides of the invention. Thus, Sso7 and polymerase domains that are modified by such methods are also part of the invention. For example, a codon for a cysteine residue can be placed at either end of a domain so that the domain can be linked by, for example, a sulfide linkage. The modification can be performed using either recombinant or chemical methods (see, e.g., Pierce Chemical Co. catalog, Rockford Ill.).

The Sso7 and polymerase domains of the recombinant fusion protein can be joined by linker domains, usually polypeptide sequences including Gly, Ser, Ala, and Val such as those described above. In some embodiments, proline residues are incorporated into the linker to prevent the formation of significant secondary structural elements by the linker.

In some embodiments, the recombinant nucleic acids the recombinant nucleic acids encoding the proteins of the invention are modified to provide preferred codons which enhance translation of the nucleic acid in a selected organism (e.g., yeast preferred codons are substituted into a coding nucleic acid for expression in yeast).

A variety of expression systems known to those of ordinary skill in the art can be used to express the protein conjugates of the invention. In some embodiments, the polynucleotide that encodes the fusion polypeptide is placed under the control of a promoter that is functional in the desired host cell. An extremely wide variety of promoters are available, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., Nature (1977) 198: 1056), the tryptophan (trp) promoter system (Goeddel et al., Nucleic Acids Res. (1980) δ: 4057), the tac promoter (DeBoer, et al., Proc. Natl. Acad. Sci. U.S.A. (1983) 80:21 25); and the lambda-derived PL promoter and N-gene ribosome binding site (Shimatake et al., Nature (1981) 292: 128). The particular promoter system is not critical to the invention, any available promoter that functions in prokaryotes can be used. Standard bacterial expression vectors include plasmids such as pBR322-based plasmids, e.g., pBLUESCRIPT, pSKF, pET23D, and fusion expression systems such as GST and LacZ. Epitope tags can also be added to recombinant proteins to provide convenient methods of isolation.

For expression of fusion polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*. These and other suitable bacterial promoters are well known in the art and are described, e.g., in Sambrook et al.

and Ausubel et al. Bacterial expression systems for expressing the proteins of the invention are available in, e.g., *E. coli*, *Bacillus* sp., and *Salmonella* (Palva et al., Gene 22:229-235 (1983); Mosbach et al., Nature 302:543-545 (1983). Kits for such expression systems are commercially available.

Eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used in the present invention. Regulated promoters can be advantageous because the host cells can be grown to high densities before expression of the fusion polypeptides is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals.

For *E. coli* and other bacterial host cells, inducible promoters are known to those of skill in the art. These include, for example, the lac promoter, the bacteriophage lambda PL promoter, the hybrid trp-lac promoter (Amann et al. (1983) Gene 25: 167; de Boer et al. (1983) Proc. Nat'l. Acad. Sci. USA 80: 21), and the bacteriophage T7 promoter (Studier et al. (1986) J. Mol. Biol.; Tabor et al. (1985) Proc. Nat'l. Acad. Sci. USA 82: 1074-8). These promoters and their use are discussed in Sambrook et al., supra.

Inducible promoters for other organisms are also well known to those of skill in the art.

These include, for example, the metallothionein promoter, the heat shock promoter, as well as many others.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), J. Biol. Chem. 263: 16297-16302.

The construction of polynucleotide constructs generally requires the use of vectors able to replicate in bacteria. Such vectors are commonly used in the art. A plethora of kits are commercially available for the purification of plasmids from bacteria (for example, EasyPrepJ, FlexiPrepJ, from Pharmacia Biotech; StrataCleanJ, from Stratagene; and, QIAexpress Expression System, Qiagen). The isolated and purified plasmids can then be further manipulated to produce other plasmids, and used to transform cells.

The fusion polypeptides can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., Bio/Technology (1984) 2: 800; Schoner et al., Bio/Technology (1985) 3: 151). Fusion polypeptides of the invention can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the recombinant fusion polypeptides can be purified according to standard procedures of the art, including ammonium sulfate precipitation, affinity columns, column chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

To facilitate purification of the fusion polypeptides of the invention, the nucleic acids that encode the fusion polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines (SEQ ID NO:63) are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

V. Methods

As discussed herein, the present invention provides conjugate proteins for use in nucleic acid amplification reactions. Such amplification reactions include without limitation polymerase chain reaction (PCR), DNA ligase chain reaction (LCR), QBeta RNA replicase, and RNA transcription-based (such as TAS and 3SR) amplification reactions as well as others known to those of skill in the art. Polymerase chain reactions that can be conducted using the compositions described herein include without limitation reverse-transcription PCR (rt-PCR) and quantitative PCR (qPCR).

As will be appreciated, any combination of the different components described herein is encompassed by the present invention, as are amplification reactions utilizing any combination of different components of the invention. For example, amplification reactions of the invention may utilize Sso7 polymerase conjugates comprising one or mutations that remove or completely abolish exonuclease activity, particularly 3'-5' exonuclease activity. Such amplification reactions may further utilize such mutant hybrid polymerases combined with hot-start antibodies. Some amplification reactions of the invention may utilize mutant hybrid polymerases comprising the D141A/E143A double point mutation combined with additives such as sarcosine or heparin. Some amplification reactions of the invention may also utilize mutant hybrid polymerases lacking 3'-5' exonuclease activity combined with hot-start antibodies and with additives such as sarcosine or heparin.

In some embodiments, dye-based qPCR detection methods are used to monitor amplification reactions utilizing components of the invention. Such detection methods generally rely on monitoring the increase in fluorescence signal due to the binding of DNA-binding dye to the amplified DNA. For example, SYBR Green I, a commonly used fluorescent DNA binding dye, binds all double—stranded DNA and detection is monitored by measuring the increase in fluorescence throughout the cycle.

In other embodiments, probe-based qPCR detection methods are used to monitor amplification reactions utilizing components of the invention. Such detection methods generally rely on the sequence-specific detection of a desired PCR product. Unlike dye-based qPCR methods that detect all double-stranded DNA, probe-based qPCR utilizes a fluorescent-labeled target-specific probe, which detects specific sequences in the amplified DNA.

VI. Reaction Mixtures

The present invention also provides reaction mixtures comprising the Sso7-polymerase conjugates of the invention. Optionally, an antibody is complexed with the polymerase. The reaction mixtures can optionally comprise one or more dNTPs, one or more oligonucleotides, a biological sample comprising a target nucleic acid, and/or a double stranded DNA binding dye or other reagent useful for PCR or primer extension reactions.

In certain aspects, it may be desirable to include an additional compound as an additive to improve efficiency in amplification reactions, including but not limited to qPCR. In some embodiments, inclusion of the additive is sufficient to increase efficiency of the polymerase by at least 5, 10, 15, 20, 25, 35, 40, or 50% or more compared to a control mixture lacking the additive.

In some embodiments, the additive is an osmolyte included in an amplification reaction of the invention to improve efficiency. Members of the osmolyte family have been shown to improve the thermal stability of proteins (Santoro, Biochemistry, 1992) as well as decrease DNA double helix stability (Chadalavada, FEBS Letters, 1997). In some embodiments, osmolytes are small molecules or compounds which are produced by living organisms in response to environmental stresses such as extreme temperatures, dehydration, or salinity and which protect their cellular components and help to maintain optimal cytosolic conditions. Osmolytes of use in the present invention may include without limitation sarcosine, trimethylamine N-oxide (TMAO), dimethylsulfoniopropionate, and trimethylglycine.

In some embodiments, concentrations of about 100 to about 1000 mM of osmolytes are used in methods and kits of the present invention. In still further embodiments, concentrations of about 50 to about 700, about 100 to about 600, about 150 to about 500, about 200 to about 400 mM, and about 300 to about 350 mM osmolytes are used in methods and kits of the invention. In some embodiments, the osmolyte used in methods, reaction mixtures, and kits of the invention is sarcosine (optionally at the above-listed concentrations).

In some embodiments, particularly in the amplification of low-copy target nucleic acids, efficiency decreases due to the binding of polymerase to non-primed double-stranded nucleic acid targets. Binding of the polymerase to the double-stranded targets will prevent those targets from denaturation, hybridizing to primers, and undergoing an amplification reaction. To improve the specificity of the polymerase for primed templates, in some embodiments reaction mixtures of the invention utilize heparin. Heparin molecules, which are negatively charged, can be included in the reaction mixture to mimic the electrostatic property of double stranded nucleic acids. The addition of heparin can, without being limited to a mechanism of action, prevent excess polymerase from binding to the double-stranded template until a single-stranded primed-template becomes available. In some exemplary embodiments, heparin is used in methods and kits of the invention at concentrations of about 50 to about 750 pg/µl. In further exemplary embodiments, heparin is used in methods and kits of the invention at concentrations of about 75 to about 700, about 100 to about 600, about 125 to about 500, about 150 to about 400, about 175 to about 300, and about 200 to about 250 pg/µl. Other molecules known in the art can be used in a similar manner to prevent non-specific binding of the polymerase to non-primed double-stranded template.

In some embodiments, the reaction mixtures comprise an agent that improves the specificity of nucleic acid amplification when added to an amplification reaction mixture prior to amplification of the target nucleic acid molecule. In some embodiments, the agent is selected from arginine (e.g., L-arginine or D-arginine), spermidine, and spermine. In some embodiments, the agent is arginine.

In some embodiments, the agent that improves the specificity of nucleic acid amplification is present in the amplification reaction mixture at a concentration of about 1 mM to about 500 mM. In some embodiments, the agent is present at a concentration of about 1 mM to about 100 mM, about 1 mM to about 75 mM, about 1 mM to about 50 mM, about 1 mM to about 25 mM, or about 5 mM to about 15 mM.

The arginine, spermidine, and/or spermine agents of the present invention may be provided as salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, and benzoates. These salts may be prepared by methods known to those skilled in art. Also included are base addition salts such as sodium, potassium, calcium, ammonium, organic amino, or magnesium salt, or a similar salt. When an agent of the present invention contains relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. In some embodiments, arginine, spermidine, and/or spermine salts are monohydrochloride, dihydrochloride, trihydrochloride, or tetrahydrochloride salts.

In some embodiments, an amplification reaction mixture of the present invention comprises: a polymerase (e.g., a polymerase-Sso7 conjugate) as described herein at a concentration of about 1 U/ml to about 75 U/ml (e.g., about 1 U/ml, 5 U/ml, 10 U/ml, 15 U/ml, 20 U/ml, 25 U/ml, 30 U/ml, 35 U/ml, 40 U/ml, 45 U/ml, 50 U/ml, 55 U/ml, 60 U/ml, 65 U/ml, 70 U/ml, or 75 U/ml); arginine, spermidine, or spermine or a salt thereof at a concentration of about 1 mM to about 100 mM (e.g., about 1 mM, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM); dNTPs at a concentration of about 0.1 mM to about 10 mM (e.g., about 0.1 mM, 0.2 mM, 0.3 mM, 0.4 mM, 0.5 mM, 0.6 mM, 0.7 mM, 0.8 mM, 0.9 mM, 1 mM, 2 mM, 3 mM, 4 mM, 5 mM, 6 mM, 7 mM, 8 mM, 9 mM, or 10 mM); magnesium, e.g., $MgCl_2$, at a concentration of about 1 mM to about 20 mM (e.g., about 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, or 20 mM); $(NH_4)_2SO_4$ at a concentration of about 10 mM to about 100 mM (e.g., about 10 mM, 20 mM, 30 mM, 40 mM, 50 mM, 60 mM, 70 mM, 80 mM, 90 mM, or 100 mM); potassium, e.g, KCl, at a concentration of about 50 mM to about 200 mM (e.g., about 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM); a buffer, e.g., Tris pH 8.5-9.5 at a concentration of about 50 mM to about 200 mM (e.g., about 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM) or a buffer (when measured at a concentration of 0.1 M) that has a change of no more than 0.027 pH units per degree C. when between 20° and 37° C. at a concentration of about 5 mM to about 200 mM (e.g., about 5 mM, 10 mM, 25 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM); a disaccharide, e.g., trehalose, at a concentration of about 100 mM to about 500 mM (e.g., about 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, or 500 mM); one or more osmolytes, e.g, sarcosine, trimethylamine N-oxide (TMAO), dimethylsulfoniopropionate, and trimethylglycine, at a concentration of about 50 mM to about 200 mM (e.g., about 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM); Tween-20 at a concentration of about 0.1% to about 0.5% (e.g., about 0.1%, 0.2%, 0.3%, 0.4%, or 0.5%); glycerol at a concentration of about 1% to about 10% (e.g., about 1%, 2%, 3%, 4%, 5%, 6%, 7%, 8%, 9%, 10%); DMSO at a concentration of about 1% to about 10% (e.g., about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%); fluorescein at a concentration of about 0.001% to about 0.01% (e.g., about 0.001%, 0.002%, 0.003%, 0.004%, 0.005%, 0.006%, 0.007%, 0.008%, 0.009%, or 0.01%); and DNA binding dye (e.g., cyanine dye) at a concentration of about 0.5× to about 5×(e.g., about 0.5×, 0.6×, 0.7×, 0.8×, 0.9×, 1×, 1.5×, 2×, 2.5×, 3×, 3.5×, 4×, 4.5×, or 5×).

It has been discovered that inclusion of POPSO in an amplification reaction can improve amplification specificity, and based on this discovery, it is believed that any buffer (e.g., POPSO) having a change of no more than 0.027 pH units per degree C. when between 20° and 37° C. will have the same effect. Thus, the reaction mixtures described above can include, e.g., HEPES ((4-(2-hydroxyethyl)-1-piperazineethanesulfonic acid)), ACES (N-(2-Acetamido)-2-aminoethanesulfonic acid), PIPES (piperazine-N,N'-bis(2-ethanesulfonic acid), MOPSO (3-(N-Morpholino)-2-hydroxypropanesulfonic Acid), BES (N,N-Bis(2-hydroxyethyl)-2-aminoethanesulfonic Acid), MOPS (3-(N-morpholino)propanesulfonic acid), TES (N-Tris(hydroxymethyl)methyl-2-aminoethanesulfonic acid), TAPSO (3-[N-Tris(hydroxymethyl)methylamino]-2-hydroxypropanesulfonic Acid), POPSO (piperazine-N,N'-bis (2-hydroxypropanesulfonic acid)), BICINE (N,N-bis(2-hydroxyethyl)glycine), TAPS(N-Tris(hydroxymethyl)methyl-3-aminopropanesulfonic acid), or AMPSO(N-(1,1-Dimethyl-2-hydroxyethyl)-3-amino-2-hydroxypropanesulfonic acid).

VII. Kits

In one aspect, the present invention provides kits for conducting nucleic acid amplification reactions. In some embodiments, such kits include a Sso7-polymerase conjugate, and optionally dNTPs, and at least one buffer (e.g., Triss or a buffer (e.g., HEPES or POPSO) having a change of no more than 0.027 pH units per degree C. when between 20° and 37° C.). Such kits may also include primers, probes, stabilizers and other additives (e.g., arginine, spermidine, spermine, heparin and/or sarcosine) to increase the efficiency of the amplification reactions. Such kits may also include one or more primers as well as instructions for conducting nucleic acid amplification reactions using the components of the kits.

In a further aspect, the present invention provides kits that include components that improve the efficiency and specificity of nucleic acid amplification reactions over reactions conducted using conventional reaction conditions and reactants. Such additional components are described further herein and include without limitation hot-start antibodies, and/or additives such as sarcosine and heparin.

EXAMPLES

The following examples are intended to illustrate, but not to limit, the claimed invention.

Example 1

A series of Sso7d-polymerase conjugates were generated based on SEQ ID NO:2 for the polymerase domain and SEQ ID NO:3 as the Sso7d domain. The Sso7d domain was mutated at positions 28 (wild-type K) or 43 (wild-type R). The resulting conjugates were tested by amplifying a template DNA molecule and detecting the resulting product with SYBR GREEN using melting temperature analysis. A two-step PCR was performed to amplify 18s amplicon (18s68) using 1 ng of HeLa cell derived cDNA as template. qPCR was performed on Bio-Rad CFX96 qPCR instrument using regular 2-step PCR protocol with 5s denaturation step at 95° C. and followed by 30s anneal-extension step at 61° C. in each amplification cycle. Forty cycles of PCR amplification were performed and followed by melt-curve analysis using 0.5° C. temperature increments with 5s hold in each step. The melt-curve analysis was used to evaluate PCR specificity, which is a technique to characterize double-stranded DNA (dsDNA) based on their dissociation (melting) behavior as they transition from dsDNA to single-stranded DNA (ssDNA) with increasing temperature (Tm). In general, target sequence was amplified by PCR prior to melt-curve analysis. According to the nucleotide sequence, length, GC content, and strand complementarity, melting of PCR products will give a single peak of specific melting temperature. Therefore, single melt-peak indicates one specific PCR product. Multiple peaks indicate the presence of non-specific products in addition to the specific one.

While the wild-type conjugate generated considerable non-specific products (i.e., two peaks in melt-curve analysis), a number of substitutions at the position corresponding to K28 resulted in improved activity, i.e., reduced non-specific polymerase activity. Mutants in which R28 was changed to any of S, T, C, P, D, E, N, or Q had improved activity (specificity) compared to the R28 wildtype. R28M and R28R were not significantly better than wildtype. The K28 variant Sso7d-polymerase conjugates tested included those having sequences according to SEQ ID NOS:35-42.

A two-step PCR was then performed to amplify beta-Actin amplicon (ActB86), using 1 ng of HeLa cell derived cDNA as template and under the same conditions as described above to evaluate PCR specificity for R43 variant Sso7d-polymerase conjugates. A number of substitutions resulted in decreased nonspecific polymerase activity. For example, mutants in which R43 was changed to any of G, A, S, T, C, V, L, I, M, F, Y, D, E, N, Q, H, K, or W had improved activity (specificity) compared to the R43 wildtype. R43M had a slight non-specific shoulder, but was still significantly improved compared to wildtype. The R43 variant Sso7-polymerase conjugates tested included those having sequences according to SEQ ID NOS:43-60.

In addition, it was discovered that non-specific polymerase activity can also be reduced by adding reagents to the PCR reaction mixture. PCR was performed to amplify 18s amplicon (18s68) using 10 ng, 1 ng, 100 pg, and 10 pg of HeLa cell derived cDNA as template. qPCR was performed using a regular 2-step PCR protocol with 5s denaturation step at 98° C. and followed by 30s anneal-extension step at 60° C. in each amplification cycle. Forty cycles of PCR amplifications were carried out and followed by melt-curve analysis as described above. The addition of L-Arginine monohydrochloride (10 mM), spermidine trihydrochloride (5 mM), or spermine tetrahydrochloride (5 or 10 mM) further reduced non-specific activity of the Sso7d-polymerase conjugate variants tested. This was further demonstrated in qPCR results using reaction mixtures containing 10 mM L-arginine monohydrochloride at different template concentrations (from 10 ng to 10 pg). Compared to the controls lacking free arginine, the corresponding reactions containing free arginine had more specific product and considerably less non-specific product at each template concentration.

Next, the effect of arginine in enhancing inhibitor tolerance of qPCR reagent mixture was tested. Amplification reaction mixtures contained an exonuclease deficient polymerase (SEQ ID NO:33) conjugated to a mutated Sso7d domain (SEQ ID NO:38) at a final concentration of about 24 U/ml and a polymerase inhibitor (one of two different chocolates (Enlveonet or Tanzanie), a common PCR inhibitor). Arginine was omitted from one set of samples and added at a concentration of 10 mM to another set of samples. The final percentage concentration of chocolate in the qPCR reaction ranged from 0-2%. PCR was performed to amplify ADAR amplicon (ADAR_162) using 1 ng of HeLa cell derived cDNA as template. qPCR was performed using regular 2-step PCR protocol with 5s denaturation step at 95° C. and followed by 30s anneal-extension step at 60° C. in each amplification cycle. Forty cycles of PCR amplifications were carried out and followed by melt-curve analysis as described above. Success of PCR amplification (as reflected by an amplification and also evaluated by the Ct value) in the presence of different concentrations of inhibitor indicates how well the reaction mixture tolerates the PCR inhibitor. For both chocolates, in the presence of higher concentrations of inhibitor, poor or no amplification was observed for the reagent mixture in the absence of arginine. In contrast, reagent mixture supplemented with arginine still exhibited good PCR amplification even in the presence of 2% inhibitor, suggesting higher inhibitor tolerance.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An Sso7 polymerase conjugate protein comprising an Sso7 domain linked to a polymerase; wherein:
    the Sso7 domain is at least 75% identical to SEQ ID NO:2;
    an amino acid of the Sso7 domain corresponding to R43 of SEQ ID NO:2 is not arginine (R); and
    the conjugate protein has a decreased non-specific amplification activity compared to an otherwise identical control conjugate protein in which the amino acid of the Sso7 domain corresponding to R43 of SEQ ID NO:2 is arginine (R).

2. The Sso7 polymerase conjugate protein of claim 1, wherein the non-specific amplification activity of the Sso7 polymerase conjugate protein is reduced by at least 10% compared to non-specific amplification activity of the control conjugate protein.

3. The Sso7 polymerase conjugate protein of claim 1, wherein the amino acid of the Sso7 domain corresponding to K28 of SEQ ID NO:2 is not lysine (K).

4. The Sso7 polymerase conjugate protein of claim 3, wherein the amino acid of the Sso7 domain corresponding to K28 of SEQ ID NO:2 is selected from the group consisting of serine (S), threonine (T), cysteine (C), proline (P), aspartic acid (D), glutamic acid (E), asparagine (N), glutamine (Q), alanine (A), phenylalanine (F), glycine (G), histidine (H), isoleucine (I), leucine (L), methionine (M), arginine (R), valine (V), tryptophan (W), and tyrosine (Y).

5. The Sso7 polymerase conjugate protein of claim 1, wherein the amino acid of the Sso7 domain corresponding to R43 of SEQ ID NO:2 is selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), glutamine (Q), serine (S), threonine (T), valine (V), tryptophan (W), tyrosine (Y), and proline (P).

6. The Sso7 polymerase conjugate protein of claim 1, wherein the polymerase substantially lacks a 3'-5' exonuclease activity.

7. The Sso7 polymerase conjugate protein of claim 1, wherein the Sso7 domain is 90% identical to the first 58 amino acids of SEQ ID NO: 2.

8. The Sso7 polymerase conjugate protein of claim 1, wherein the Sso7 domain is at least 90% identical to SEQ ID NO:2.

9. The Sso7 polymerase conjugate protein of claim 1, wherein the polymerase is at least 60% identical to SEQ ID NO:33 or SEQ ID NO:61.

10. The Sso7 polymerase conjugate protein of claim 9, wherein the polymerase comprises SEQ ID NO: 33 or SEQ ID NO:61.

11. The Sso7 polymerase conjugate protein of claim 1, wherein the polymerase domain has thermally stable polymerase activity.

12. The Sso7 polymerase conjugate protein of claim 11, wherein the polymerase domain is a family A polymerase domain.

13. The Sso7 polymerase conjugate protein of claim 12, wherein the polymerase domain is a ΔTaq polymerase domain.

14. The Sso7 polymerase conjugate protein of claim 11, wherein the polymerase domain is a family B polymerase domain.

15. The Sso7 polymerase conjugate protein of claim 14, wherein the polymerase domain is from *Pyrococcus*.

16. A reaction mixture comprising the Sso7 polymerase conjugate protein of claim 1.

17. The reaction mixture of claim 16, further comprising at least one of or more oligonucleotide primers, one or more detectably-labeled oligonucleotide probe, a buffer, nucleoside triphosphates, a salt, a DNA binding dye, or a stabilizer.

18. A kit comprising the Sso7 polymerase conjugate protein of claim 1.

19. The kit of claim 18, further comprising in the same or a different container that contains the conjugate protein, at least one of one or more oligonucleotide primers, one or more detectably-labeled oligonucleotide probe, a buffer, nucleoside triphosphates, a salt, a DNA binding dye, or a stabilizer.

20. The Sso7 polymerase conjugate protein of claim 1, wherein the amino acid of the Sso7 domain corresponding to R43 of SEQ ID NO: 2 is selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), glutamine (Q), serine (S), threonine (T), valine (V), tryptophan (W), tyrosine (Y).

* * * * *

SEQUENCE LISTING

```
<160> NUMBER OF SEQ ID NOS: 63

<210> SEQ ID NO 1
<211> LENGTH: 192
<212> TYPE: DNA
<213> ORGANISM: Artificial Sequence
<220> FEATURE:
<223> OTHER INFORMATION: synthetic Sso7d/Ssh7A/SsoP2 DNA binding domain
      coding sequence

<400> SEQUENCE: 1
atggcaaccg taaagttcaa gtacaaaggc gaagaaaaag aggtagacat ctccaagatc      60
aagaaagtat ggcgtgtggg caagatgatc tccttcacct acgacgaggg cggtggcaag     120
accggccgtg gtgcggtaag cgaaaaggac gcgccgaagg agctgctgca gatgctggag     180
aagcagaaaa ag                                                         192

<210> SEQ ID NO 2
<211> LENGTH: 64
<212> TYPE: PRT
<213> ORGANISM: Sulfolobus acidocaldarius
<220> FEATURE:
<223> OTHER INFORMATION: Sulfolobus acidocaldarius Sso7d,
      Sso7d/Ssh7A/SsoP2, DNA-binding protein 7d, chain A,
      hyperthermophile protein-DNA complex;
      Sulfolobus solfataricus strain P2 Sso7d
```

```
<400> SEQUENCE: 2

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 3
<211> LENGTH: 64
<212> TYPE: PRT
<213> ORGANISM: Sulfolobus shibatae
<220> FEATURE:
<223> OTHER INFORMATION: Ssh7b, DNA-binding protein 7b

<400> SEQUENCE: 3

Met Val Thr Val Lys Phe Lys Tyr Lys Gly Glu Glu Lys Glu Val Asp
1               5                   10                  15

Thr Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 4
<211> LENGTH: 66
<212> TYPE: PRT
<213> ORGANISM: Sulfolobus sp.
<220> FEATURE:
<223> OTHER INFORMATION: Sulfolobus sp. Sac7d, DNA-binding protein
      7d, helix stabilizing protein; Sulfolobus acidocaldarius strain
      DSM 639 Sac7d, DNA-binding protein 7d, Saci_0064

<400> SEQUENCE: 4

Met Val Lys Val Lys Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 5
<211> LENGTH: 65
<212> TYPE: PRT
<213> ORGANISM: Sulfolobus acidocaldarius
<220> FEATURE:
<223> OTHER INFORMATION: Sulfolobus acidocaldarius strain DSM 639 Sac7e,
      DNA-binding protein 7e, Saci_0362

<400> SEQUENCE: 5

Met Ala Lys Val Arg Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30
```

Thr Tyr Asp Asp Asn Gly Lys Thr Gly Arg Gly Ala Val Ser Glu Lys
        35                  40                  45

Asp Ala Pro Lys Glu Leu Met Asp Met Leu Ala Arg Ala Glu Lys Lys
    50                  55                  60

Lys
65

<210> SEQ ID NO 6
<211> LENGTH: 64
<212> TYPE: PRT
<213> ORGANISM: Sulfolobus tokodaii
<220> FEATURE:
<223> OTHER INFORMATION: Sulfolobus tokodaii strain 7 Sto7e, DNA-
      binding protein 7, STS077, STK_06395, STS226, STK_20955

<400> SEQUENCE: 6

Met Val Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Gln Met Leu Glu Lys Ser Gly Lys Lys
    50                  55                  60

<210> SEQ ID NO 7
<211> LENGTH: 64
<212> TYPE: PRT
<213> ORGANISM: Artificial Sequence
<220> FEATURE:
<223> OTHER INFORMATION: synthetic Sso7 domain Sso7d-K28S

<400> SEQUENCE: 7

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 8
<211> LENGTH: 64
<212> TYPE: PRT
<213> ORGANISM: Artificial Sequence
<220> FEATURE:
<223> OTHER INFORMATION: synthetic Sso7 domain Sso7d-K28T

<400> SEQUENCE: 8

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Thr Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 9

-continued

```
<211> LENGTH: 64
<212> TYPE: PRT
<213> ORGANISM: Artificial Sequence
<220> FEATURE:
<223> OTHER INFORMATION: synthetic Sso7 domain Sso7d-K28C

<400> SEQUENCE: 9

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Cys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 10
<211> LENGTH: 64
<212> TYPE: PRT
<213> ORGANISM: Artificial Sequence
<220> FEATURE:
<223> OTHER INFORMATION: synthetic Sso7 domain Sso7d-K28P

<400> SEQUENCE: 10

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Pro Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 11
<211> LENGTH: 64
<212> TYPE: PRT
<213> ORGANISM: Artificial Sequence
<220> FEATURE:
<223> OTHER INFORMATION: synthetic Sso7 domain Sso7d-K28D

<400> SEQUENCE: 11

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Asp Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 12
<211> LENGTH: 64
<212> TYPE: PRT
<213> ORGANISM: Artificial Sequence
<220> FEATURE:
<223> OTHER INFORMATION: synthetic Sso7 domain Sso7d-K28E

<400> SEQUENCE: 12

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Glu Met Ile Ser Phe
            20                  25                  30
```

```
Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
 50                  55                  60
```

<210> SEQ ID NO 13
<211> LENGTH: 64
<212> TYPE: PRT
<213> ORGANISM: Artificial Sequence
<220> FEATURE:
<223> OTHER INFORMATION: synthetic Sso7 domain Sso7d-K28N

<400> SEQUENCE: 13

```
Met Ala Thr Val Lys Phe Lys Tyr Lys Gly Glu Glu Lys Glu Val Asp
 1               5                   10                  15

Ile Ser Lys Ile Lys Lys Val Trp Arg Val Gly Asn Met Ile Ser Phe
                20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
 50                  55                  60
```

<210> SEQ ID NO 14
<211> LENGTH: 64
<212> TYPE: PRT
<213> ORGANISM: Artificial Sequence
<220> FEATURE:
<223> OTHER INFORMATION: synthetic Sso7 domain Sso7d-K28Q

<400> SEQUENCE: 14

```
Met Ala Thr Val Lys Phe Lys Tyr Lys Gly Glu Glu Lys Glu Val Asp
 1               5                   10                  15

Ile Ser Lys Ile Lys Lys Val Trp Arg Val Gly Gln Met Ile Ser Phe
                20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
 50                  55                  60
```

<210> SEQ ID NO 15
<211> LENGTH: 64
<212> TYPE: PRT
<213> ORGANISM: Artificial Sequence
<220> FEATURE:
<223> OTHER INFORMATION: synthetic Sso7 domain Sso7d-R43G

<400> SEQUENCE: 15

```
Met Ala Thr Val Lys Phe Lys Tyr Lys Gly Glu Glu Lys Glu Val Asp
 1               5                   10                  15

Ile Ser Lys Ile Lys Lys Val Trp Arg Val Gly Ser Met Ile Ser Phe
                20                  25                  30

Thr Tyr Asp Glu Gly Gly Gly Lys Thr Gly Gly Gly Ala Val Ser Glu
        35                  40                  45

Lys Asp Ala Pro Lys Glu Leu Leu Gln Met Leu Glu Lys Gln Lys Lys
 50                  55                  60
```

<210> SEQ ID NO 16
<211> LENGTH: 64
<212> TYPE: PRT
<213> ORGANISM: Artificial Sequence
<220> FEATURE:

<223> OTHER INFORMATION: synthetic Sso7 domain Sso7d-R43A

<400> SEQUENCE: 16

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Ala Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 17
<211> LENGTH: 64
<212> TYPE: PRT
<213> ORGANISM: Artificial Sequence
<220> FEATURE:
<223> OTHER INFORMATION: synthetic Sso7 domain Sso7d-R43S

<400> SEQUENCE: 17

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Ser Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 18
<211> LENGTH: 64
<212> TYPE: PRT
<213> ORGANISM: Artificial Sequence
<220> FEATURE:
<223> OTHER INFORMATION: synthetic Sso7 domain Sso7d-R43T

<400> SEQUENCE: 18

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Thr Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 19
<211> LENGTH: 64
<212> TYPE: PRT
<213> ORGANISM: Artificial Sequence
<220> FEATURE:
<223> OTHER INFORMATION: synthetic Sso7 domain Sso7d-R43C

<400> SEQUENCE: 19

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Cys Gly Ala Val Ser Glu
        35                  40                  45

Lys Asp Ala Pro Lys Glu Leu Leu Gln Met Leu Glu Lys Gln Lys Lys
            50                  55                  60

<210> SEQ ID NO 20
<211> LENGTH: 64
<212> TYPE: PRT
<213> ORGANISM: Artificial Sequence
<220> FEATURE:
<223> OTHER INFORMATION: synthetic Sso7 domain Sso7d-R43V

<400> SEQUENCE: 20

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Val Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 21
<211> LENGTH: 64
<212> TYPE: PRT
<213> ORGANISM: Artificial Sequence
<220> FEATURE:
<223> OTHER INFORMATION: synthetic Sso7 domain Sso7d-R43L

<400> SEQUENCE: 21

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Leu Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 22
<211> LENGTH: 64
<212> TYPE: PRT
<213> ORGANISM: Artificial Sequence
<220> FEATURE:
<223> OTHER INFORMATION: synthetic Sso7 domain Sso7d-R43I

<400> SEQUENCE: 22

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Ile Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 23
<211> LENGTH: 64
<212> TYPE: PRT
<213> ORGANISM: Artificial Sequence
<220> FEATURE:
<223> OTHER INFORMATION: synthetic Sso7 domain Sso7d-R43M

<400> SEQUENCE: 23

```
Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Met Gly Ala Val Ser Glu
        35                  40                  45

Lys Asp Ala Pro Lys Glu Leu Leu Gln Met Leu Glu Lys Gln Lys Lys
    50                  55                  60
```

<210> SEQ ID NO 24
<211> LENGTH: 64
<212> TYPE: PRT
<213> ORGANISM: Artificial Sequence
<220> FEATURE:
<223> OTHER INFORMATION: synthetic Sso7 domain Sso7d-R43F

<400> SEQUENCE: 24

```
Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Phe Gly Ala Val Ser Glu
        35                  40                  45

Lys Asp Ala Pro Lys Glu Leu Leu Gln Met Leu Glu Lys Gln Lys Lys
    50                  55                  60
```

<210> SEQ ID NO 25
<211> LENGTH: 64
<212> TYPE: PRT
<213> ORGANISM: Artificial Sequence
<220> FEATURE:
<223> OTHER INFORMATION: synthetic Sso7 domain Sso7d-R43Y

<400> SEQUENCE: 25

```
Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Tyr Gly Ala Val Ser Glu
        35                  40                  45

Lys Asp Ala Pro Lys Glu Leu Leu Gln Met Leu Glu Lys Gln Lys Lys
    50                  55                  60
```

<210> SEQ ID NO 26
<211> LENGTH: 64
<212> TYPE: PRT
<213> ORGANISM: Artificial Sequence
<220> FEATURE:
<223> OTHER INFORMATION: synthetic Sso7 domain Sso7d-R43W

<400> SEQUENCE: 26

```
Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Trp Gly Ala Val Ser Glu
        35                  40                  45

Lys Asp Ala Pro Lys Glu Leu Leu Gln Met Leu Glu Lys Gln Lys Lys
    50                  55                  60
```

-continued

```
<210> SEQ ID NO 27
<211> LENGTH: 64
<212> TYPE: PRT
<213> ORGANISM: Artificial Sequence
<220> FEATURE:
<223> OTHER INFORMATION: synthetic Sso7 domain Sso7d-R43D

<400> SEQUENCE: 27

Met Ala Thr Val Lys Phe Lys Tyr Lys Gly Glu Glu Lys Glu Val Asp
 1               5                  10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Asp Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 28
<211> LENGTH: 64
<212> TYPE: PRT
<213> ORGANISM: Artificial Sequence
<220> FEATURE:
<223> OTHER INFORMATION: synthetic Sso7 domain Sso7d-R43E

<400> SEQUENCE: 28

Met Ala Thr Val Lys Phe Lys Tyr Lys Gly Glu Glu Lys Glu Val Asp
 1               5                  10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Glu Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 29
<211> LENGTH: 64
<212> TYPE: PRT
<213> ORGANISM: Artificial Sequence
<220> FEATURE:
<223> OTHER INFORMATION: synthetic Sso7 domain Sso7d-R43N

<400> SEQUENCE: 29

Met Ala Thr Val Lys Phe Lys Tyr Lys Gly Glu Glu Lys Glu Val Asp
 1               5                  10                  15

Ile Ser Lys Ile Lys Lys Val Trp Arg Val Gly Ser Met Ile Ser Phe
            20                  25                  30

Thr Tyr Asp Glu Gly Gly Gly Lys Thr Gly Asn Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 30
<211> LENGTH: 64
<212> TYPE: PRT
<213> ORGANISM: Artificial Sequence
<220> FEATURE:
<223> OTHER INFORMATION: synthetic Sso7 domain Sso7d-R43Q

<400> SEQUENCE: 30

Met Ala Thr Val Lys Phe Lys Tyr Lys Gly Glu Glu Lys Glu Val Asp
 1               5                  10                  15

Ile Ser Lys Ile Lys Lys Val Trp Arg Val Gly Ser Met Ile Ser Phe
```

```
                20                  25                  30

Thr Tyr Asp Glu Gly Gly Gly Lys Thr Gly Gln Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 31
<211> LENGTH: 64
<212> TYPE: PRT
<213> ORGANISM: Artificial Sequence
<220> FEATURE:
<223> OTHER INFORMATION: synthetic Sso7 domain Sso7d-R43H

<400> SEQUENCE: 31

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
                20                  25                  30

Thr Tyr Asp Glu Gly Gly Gly Lys Thr Gly His Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 32
<211> LENGTH: 64
<212> TYPE: PRT
<213> ORGANISM: Artificial Sequence
<220> FEATURE:
<223> OTHER INFORMATION: synthetic Sso7 domain Sso7d-R43K

<400> SEQUENCE: 32

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Ser Met Ile Ser Phe
                20                  25                  30

Thr Tyr Asp Glu Gly Gly Gly Lys Thr Gly Lys Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 33
<211> LENGTH: 775
<212> TYPE: PRT
<213> ORGANISM: Artificial Sequence
<220> FEATURE:
<223> OTHER INFORMATION: synthetic DNA polymerase lacking 3'-5'
      exonuclease activity

<400> SEQUENCE: 33

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
                20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
```

-continued

```
                85                  90                  95
Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Ala Ile Ala Thr
            130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
                180                 185                 190

Arg Phe Leu Lys Ile Ile Arg Glu Lys Asp Pro Asp Ile Ile Ile Thr
            195                 200                 205

Tyr Asn Gly Asp Ser Phe Asp Leu Pro Tyr Leu Ala Lys Arg Ala Glu
            210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Thr Gly Glu Gly
            290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
            370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
                420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Lys Ile
            450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510
```

```
Ser Val Thr Ala Trp Gly Arg Glu Tyr Ile Glu Phe Val Trp Lys Glu
    515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
        755                 760                 765

Trp Leu Asn Ile Lys Lys Ser
    770                 775

<210> SEQ ID NO 34
<211> LENGTH: 775
<212> TYPE: PRT
<213> ORGANISM: Artificial Sequence
<220> FEATURE:
<223> OTHER INFORMATION: synthetic DNA polymerase having 3'-5'
      exonuclease activity

<400> SEQUENCE: 34

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
```

```
                     85                  90                  95
Arg Glu Lys Ile Arg Glu His Ser Ala Val Val Asp Ile Phe Glu Tyr
                100                 105                 110
Asp Ile Pro Phe Ala Lys Arg Tyr Leu Ile Asp Lys Gly Leu Ile Pro
                115                 120                 125
Met Glu Gly Asp Glu Glu Leu Lys Leu Leu Ala Phe Asp Ile Glu Thr
            130                 135                 140
Leu Tyr His Glu Gly Glu Glu Phe Gly Lys Gly Pro Ile Ile Met Ile
145                 150                 155                 160
Ser Tyr Ala Asp Glu Glu Glu Ala Lys Val Ile Thr Trp Lys Lys Ile
                165                 170                 175
Asp Leu Pro Tyr Val Glu Val Val Ser Ser Glu Arg Glu Met Ile Lys
                180                 185                 190
Arg Phe Leu Lys Ile Ile Arg Glu Lys Asp Pro Asp Ile Ile Ile Thr
                195                 200                 205
Tyr Asn Gly Asp Ser Phe Asp Leu Pro Tyr Leu Ala Lys Arg Ala Glu
            210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Arg Arg Thr Ile Asn Leu Pro Thr
                260                 265                 270
Tyr Thr Leu Glu Ala Val Tyr Glu Ala Ile Phe Gly Lys Pro Lys Glu
                275                 280                 285
Lys Val Tyr Ala Asp Glu Ile Ala Lys Ala Trp Glu Thr Gly Glu Gly
            290                 295                 300
Leu Glu Arg Val Ala Lys Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Pro Leu Trp Asp Val Ser Arg Ser Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Arg Glu Tyr Glu Arg Arg Leu Arg Glu Ser
            370                 375                 380
Tyr Ala Gly Gly Phe Val Lys Glu Pro Glu Lys Gly Leu Trp Glu Asn
385                 390                 395                 400
Ile Val Ser Leu Asp Phe Arg Ala Leu Tyr Pro Ser Ile Ile Ile Thr
                405                 410                 415
His Asn Val Ser Pro Asp Thr Leu Asn Arg Glu Gly Cys Arg Asn Tyr
                420                 425                 430
Asp Val Ala Pro Glu Val Gly His Lys Phe Cys Lys Asp Phe Pro Gly
                435                 440                 445
Phe Ile Pro Ser Leu Leu Lys Arg Leu Leu Asp Glu Arg Gln Lys Ile
            450                 455                 460
Lys Thr Lys Met Lys Ala Ser Gln Asp Pro Ile Glu Lys Ile Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
```

Ser Val Thr Ala Trp Gly Arg Glu Tyr Ile Glu Phe Val Trp Lys Glu
    515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
                580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Trp Gln Lys Thr Lys Gln Thr Gly Leu Thr Ser
            755                 760                 765

Trp Leu Asn Ile Lys Lys Ser
        770                 775

<210> SEQ ID NO 35
<211> LENGTH: 844
<212> TYPE: PRT
<213> ORGANISM: Artificial Sequence
<220> FEATURE:
<223> OTHER INFORMATION: synthetic polymerase + linker + Sso7d-K28S
      polymerase conjugate

<400> SEQUENCE: 35

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
                20                  25                  30

Thr Phe Arg Pro Tyr Ile Tyr Ala Leu Leu Lys Asp Asp Ser Lys Ile
            35                  40                  45

Glu Glu Val Lys Lys Ile Thr Ala Glu Arg His Gly Lys Ile Val Arg
        50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile

```
                     85                  90                  95
Arg Glu Lys Ile Arg Glu His Ser Ala Val Val Asp Ile Phe Glu Tyr
                100                 105                 110
Asp Ile Pro Phe Ala Lys Arg Tyr Leu Ile Asp Lys Gly Leu Ile Pro
                115                 120                 125
Met Glu Gly Asp Glu Glu Leu Lys Leu Leu Ala Phe Ala Ile Ala Thr
            130                 135                 140
Leu Tyr His Glu Gly Glu Glu Phe Gly Lys Gly Pro Ile Ile Met Ile
145                 150                 155                 160
Ser Tyr Ala Asp Glu Glu Glu Ala Lys Val Ile Thr Trp Lys Lys Ile
                165                 170                 175
Asp Leu Pro Tyr Val Glu Val Val Ser Ser Glu Arg Glu Met Ile Lys
                180                 185                 190
Arg Phe Leu Lys Ile Ile Arg Glu Lys Asp Pro Asp Ile Ile Ile Thr
                195                 200                 205
Tyr Asn Gly Asp Ser Phe Asp Leu Pro Tyr Leu Ala Lys Arg Ala Glu
            210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Arg Arg Thr Ile Asn Leu Pro Thr
                260                 265                 270
Tyr Thr Leu Glu Ala Val Tyr Glu Ala Ile Phe Gly Lys Pro Lys Glu
            275                 280                 285
Lys Val Tyr Ala Asp Glu Ile Ala Lys Ala Trp Glu Thr Gly Glu Gly
            290                 295                 300
Leu Glu Arg Val Ala Lys Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
            355                 360                 365
Pro Asn Lys Pro Asp Glu Arg Glu Tyr Glu Arg Arg Leu Arg Glu Ser
            370                 375                 380
Tyr Ala Gly Gly Phe Val Lys Glu Pro Glu Lys Gly Leu Trp Glu Asn
385                 390                 395                 400
Ile Val Ser Leu Asp Phe Arg Ala Leu Tyr Pro Ser Ile Ile Ile Thr
                405                 410                 415
His Asn Val Ser Pro Asp Thr Leu Asn Arg Glu Gly Cys Arg Asn Tyr
            420                 425                 430
Asp Val Ala Pro Glu Val Gly His Lys Phe Cys Lys Asp Phe Pro Gly
            435                 440                 445
Phe Ile Pro Ser Leu Leu Lys Arg Leu Leu Asp Glu Arg Gln Lys Ile
        450                 455                 460
Lys Thr Lys Met Lys Ala Ser Gln Asp Pro Ile Glu Lys Ile Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
```

Ser Val Thr Ala Trp Gly Arg Glu Tyr Ile Glu Phe Val Trp Lys Glu
                515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Lys Ser Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
        580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
        610                 615                 620

Ala Arg Val Leu Glu Ala Ile Leu Lys His Gly Asn Val Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Trp Gln Lys Thr Lys Gln Thr Gly Leu Thr Ser
        755                 760                 765

Trp Leu Asn Ile Lys Lys Ser Gly Thr Gly Gly Gly Ala Thr Val
        770                 775                 780

Lys Phe Lys Tyr Lys Gly Glu Glu Lys Glu Val Asp Ile Ser Lys Ile
785                 790                 795                 800

Lys Lys Val Trp Arg Val Gly Ser Met Ile Ser Phe Thr Tyr Asp Glu
                805                 810                 815

Gly Gly Gly Lys Thr Gly Arg Gly Ala Val Ser Glu Lys Asp Ala Pro
        820                 825                 830

Lys Glu Leu Leu Gln Met Leu Glu Lys Gln Lys Lys
        835                 840

<210> SEQ ID NO 36
<211> LENGTH: 844
<212> TYPE: PRT
<213> ORGANISM: Artificial Sequence
<220> FEATURE:
<223> OTHER INFORMATION: synthetic polymerase + linker + Sso7d-K28T
      polymerase conjugate

<400> SEQUENCE: 36

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg

```
            20                  25                  30
Thr Phe Arg Pro Tyr Ile Tyr Ala Leu Leu Lys Asp Asp Ser Lys Ile
        35                  40                  45
Glu Glu Val Lys Lys Ile Thr Ala Glu Arg His Gly Lys Ile Val Arg
    50                  55                  60
Ile Val Asp Ala Glu Lys Val Glu Lys Lys Phe Leu Gly Arg Pro Ile
65                  70                  75                  80
Thr Val Trp Arg Leu Tyr Phe Glu His Pro Gln Asp Val Pro Thr Ile
                85                  90                  95
Arg Glu Lys Ile Arg Glu His Ser Ala Val Val Asp Ile Phe Glu Tyr
            100                 105                 110
Asp Ile Pro Phe Ala Lys Arg Tyr Leu Ile Asp Lys Gly Leu Ile Pro
        115                 120                 125
Met Glu Gly Asp Glu Glu Leu Lys Leu Leu Ala Phe Ala Ile Ala Thr
    130                 135                 140
Leu Tyr His Glu Gly Glu Glu Phe Gly Lys Gly Pro Ile Ile Met Ile
145                 150                 155                 160
Ser Tyr Ala Asp Glu Glu Glu Ala Lys Val Ile Thr Trp Lys Lys Ile
                165                 170                 175
Asp Leu Pro Tyr Val Glu Val Val Ser Ser Glu Arg Glu Met Ile Lys
            180                 185                 190
Arg Phe Leu Lys Ile Ile Arg Glu Lys Asp Pro Asp Ile Ile Ile Thr
        195                 200                 205
Tyr Asn Gly Asp Ser Phe Asp Leu Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Thr Gly Glu Gly
    290                 295                 300
Leu Glu Arg Val Ala Lys Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
    370                 375                 380
Tyr Ala Gly Gly Phe Val Lys Glu Pro Glu Lys Gly Leu Trp Glu Asn
385                 390                 395                 400
Ile Val Ser Leu Asp Phe Arg Ala Leu Tyr Pro Ser Ile Ile Ile Thr
                405                 410                 415
His Asn Val Ser Pro Asp Thr Leu Asn Arg Glu Gly Cys Arg Asn Tyr
            420                 425                 430
Asp Val Ala Pro Glu Val Gly His Lys Phe Cys Lys Asp Phe Pro Gly
        435                 440                 445
```

-continued

```
Phe Ile Pro Ser Leu Leu Lys Arg Leu Leu Asp Glu Arg Gln Lys Ile
    450                 455                 460
Lys Thr Lys Met Lys Ala Ser Gln Asp Pro Ile Glu Lys Ile Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Trp Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Lys Ser Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Lys Tyr Ala Leu Ile Asp Glu Glu Gly Lys Ile Ile Thr Arg Gly
        595                 600                 605
Leu Glu Ile Val Arg Arg Asp Trp Ser Glu Ile Ala Lys Glu Thr Gln
    610                 615                 620
Ala Arg Val Leu Glu Ala Ile Leu Lys His Gly Asn Val Glu Glu Ala
625                 630                 635                 640
Val Arg Ile Val Lys Glu Val Thr Gln Lys Leu Ser Lys Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Arg Leu Ala
        675                 680                 685
Ala Lys Gly Val Lys Ile Lys Pro Gly Met Val Ile Gly Tyr Ile Val
    690                 695                 700
Leu Arg Gly Asp Gly Pro Ile Ser Asn Arg Ala Ile Leu Ala Glu Glu
705                 710                 715                 720
Tyr Asp Pro Arg Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Trp Gln Lys Thr Lys Gln Thr Gly Leu Thr Ser
        755                 760                 765
Trp Leu Asn Ile Lys Lys Ser Gly Thr Gly Gly Gly Ala Thr Val
    770                 775                 780
Lys Phe Lys Tyr Lys Gly Glu Glu Lys Glu Val Asp Ile Ser Lys Ile
785                 790                 795                 800
Lys Lys Val Trp Arg Val Gly Thr Met Ile Ser Phe Thr Tyr Asp Glu
                805                 810                 815
Gly Gly Gly Lys Thr Gly Arg Gly Ala Val Ser Glu Lys Asp Ala Pro
            820                 825                 830
Lys Glu Leu Leu Gln Met Leu Glu Lys Gln Lys Lys
        835                 840

<210> SEQ ID NO 37
<211> LENGTH: 844
```

<212> TYPE: PRT
<213> ORGANISM: Artificial Sequence
<220> FEATURE:
<223> OTHER INFORMATION: synthetic polymerase + linker + Sso7d-K28C
      polymerase conjugate

<400> SEQUENCE: 37

Met Ile Leu Asp Ala Asp Tyr Ile Thr Glu Glu Gly Lys Pro Val Ile
 1               5                  10                  15

Arg Leu Phe Lys Lys Glu Asn Gly Glu Phe Lys Ile Glu His Asp Arg
             20                  25                  30

Thr Phe Arg Pro Tyr Ile Tyr Ala Leu Leu Lys Asp Asp Ser Lys Ile
         35                  40                  45

Glu Glu Val Lys Lys Ile Thr Ala Glu Arg His Gly Lys Ile Val Arg
 50                  55                  60

Ile Val Asp Ala Glu Lys Val Glu Lys Lys Phe Leu Gly Arg Pro Ile
 65                  70                  75                  80

Thr Val Trp Arg Leu Tyr Phe Glu His Pro Gln Asp Val Pro Thr Ile
             85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Ala Ile Ala Thr
130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
            165                 170                 175

Asp Leu Pro Tyr Val Glu Val Val Ser Ser Glu Arg Glu Met Ile Lys
        180                 185                 190

Arg Phe Leu Lys Ile Ile Arg Glu Lys Asp Pro Asp Ile Ile Ile Thr
    195                 200                 205

Tyr Asn Gly Asp Ser Phe Asp Leu Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Arg Arg Thr Ile Asn Leu Pro Thr
        260                 265                 270

Tyr Thr Leu Glu Ala Val Tyr Glu Ala Ile Phe Gly Lys Pro Lys Glu
    275                 280                 285

Lys Val Tyr Ala Asp Glu Ile Ala Lys Ala Trp Glu Thr Gly Glu Gly
290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
            325                 330                 335

Val Gly Gln Pro Leu Trp Asp Val Ser Arg Ser Ser Thr Gly Asn Leu
        340                 345                 350

Val Glu Trp Phe Leu Leu Arg Lys Ala Tyr Glu Arg Asn Glu Leu Ala
    355                 360                 365

Pro Asn Lys Pro Asp Glu Arg Glu Tyr Glu Arg Arg Leu Arg Glu Ser
370                 375                 380

```
                                      -continued

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
        755                 760                 765

Trp Leu Asn Ile Lys Lys Ser Gly Thr Gly Gly Gly Ala Thr Val
    770                 775                 780

Lys Phe Lys Tyr Lys Gly Glu Glu Lys Glu Val Asp Ile Ser Lys Ile
785                 790                 795                 800
```

-continued

```
Lys Lys Val Trp Arg Val Gly Cys Met Ile Ser Phe Thr Tyr Asp Glu
                805                 810                 815
Gly Gly Gly Lys Thr Gly Arg Gly Ala Val Ser Glu Lys Asp Ala Pro
            820                 825                 830
Lys Glu Leu Leu Gln Met Leu Glu Lys Gln Lys Lys
        835                 840
```

<210> SEQ ID NO 38
<211> LENGTH: 844
<212> TYPE: PRT
<213> ORGANISM: Artificial Sequence
<220> FEATURE:
<223> OTHER INFORMATION: synthetic polymerase + linker + Sso7d-K28P
      polymerase conjugate

<400> SEQUENCE: 38

```
Met Ile Leu Asp Ala Asp Tyr Ile Thr Glu Glu Gly Lys Pro Val Ile
  1               5                  10                  15
Arg Leu Phe Lys Lys Glu Asn Gly Glu Phe Lys Ile Glu His Asp Arg
             20                  25                  30
Thr Phe Arg Pro Tyr Ile Tyr Ala Leu Leu Lys Asp Asp Ser Lys Ile
         35                  40                  45
Glu Glu Val Lys Lys Ile Thr Ala Glu Arg His Gly Lys Ile Val Arg
     50                  55                  60
Ile Val Asp Ala Glu Lys Val Glu Lys Lys Phe Leu Gly Arg Pro Ile
65                  70                  75                  80
Thr Val Trp Arg Leu Tyr Phe Glu His Pro Gln Asp Val Pro Thr Ile
                 85                  90                  95
Arg Glu Lys Ile Arg Glu His Ser Ala Val Val Asp Ile Phe Glu Tyr
            100                 105                 110
Asp Ile Pro Phe Ala Lys Arg Tyr Leu Ile Asp Lys Gly Leu Ile Pro
        115                 120                 125
Met Glu Gly Asp Glu Glu Leu Lys Leu Leu Ala Phe Ala Ile Ala Thr
    130                 135                 140
Leu Tyr His Glu Gly Glu Glu Phe Gly Lys Gly Pro Ile Ile Met Ile
145                 150                 155                 160
Ser Tyr Ala Asp Glu Glu Glu Ala Lys Val Ile Thr Trp Lys Lys Ile
                165                 170                 175
Asp Leu Pro Tyr Val Glu Val Val Ser Ser Glu Arg Glu Met Ile Lys
            180                 185                 190
Arg Phe Leu Lys Ile Ile Arg Glu Lys Asp Pro Asp Ile Ile Ile Thr
        195                 200                 205
Tyr Asn Gly Asp Ser Phe Asp Leu Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Thr Gly Glu Gly
    290                 295                 300
Leu Glu Arg Val Ala Lys Tyr Ser Met Glu Asp Ala Lys Ala Thr Tyr
305                 310                 315                 320
```

```
Glu Leu Gly Lys Glu Phe Pro Met Glu Ala Gln Leu Ser Arg Leu
            325                 330                 335

Val Gly Gln Pro Leu Trp Asp Val Ser Arg Ser Thr Gly Asn Leu
        340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
                420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Lys Ile
        450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735
```

```
Gln Val Leu Pro Ala Val Leu Arg Ile Leu Glu Gly Phe Gly Tyr Arg
                740                 745                 750

Lys Glu Asp Leu Arg Trp Gln Lys Thr Lys Gln Thr Gly Leu Thr Ser
            755                 760                 765

Trp Leu Asn Ile Lys Lys Ser Gly Thr Gly Gly Gly Gly Ala Thr Val
        770                 775                 780

Lys Phe Lys Tyr Lys Gly Glu Glu Lys Glu Val Asp Ile Ser Lys Ile
785                 790                 795                 800

Lys Lys Val Trp Arg Val Gly Pro Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
        835                 840

<210> SEQ ID NO 39
<211> LENGTH: 844
<212> TYPE: PRT
<213> ORGANISM: Artificial Sequence
<220> FEATURE:
<223> OTHER INFORMATION: synthetic polymerase + linker + Sso7d-K28D
      polymerase conjugate

<400> SEQUENCE: 39

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Ile Ile Arg Glu Lys Asp Pro Asp Ile Ile Ile Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255
```

-continued

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
290                 295                 300

Leu Glu Arg Val Ala Lys Tyr Ser Met Glu Asp Ala Lys Ala Thr Tyr
305                 310                 315                 320

Glu Leu Gly Lys Glu Phe Pro Met Glu Ala Gln Leu Ser Arg Leu
                325                 330                 335

Val Gly Gln Pro Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Thr
                405                 410                 415

His Asn Val Ser Pro Asp Thr Leu Asn Arg Glu Gly Cys Arg Asn Tyr
                420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

```
Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Ile Glu Asn
            725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
            755                 760                 765

Trp Leu Asn Ile Lys Lys Ser Gly Thr Gly Gly Gly Ala Thr Val
            770                 775                 780

Lys Phe Lys Tyr Lys Gly Glu Glu Lys Glu Val Asp Ile Ser Lys Ile
785                 790                 795                 800

Lys Lys Val Trp Arg Val Gly Asp Met Ile Ser Phe Thr Tyr Asp Glu
                    805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
            835                 840

<210> SEQ ID NO 40
<211> LENGTH: 844
<212> TYPE: PRT
<213> ORGANISM: Artificial Sequence
<220> FEATURE:
<223> OTHER INFORMATION: synthetic polymerase + linker + Sso7d-K28E
      polymerase conjugate

<400> SEQUENCE: 40

Met Ile Leu Asp Ala Asp Tyr Ile Thr Glu Glu Gly Lys Pro Val Ile
  1               5                  10                  15

Arg Leu Phe Lys Lys Glu Asn Gly Glu Phe Lys Ile Glu His Asp Arg
             20                  25                  30

Thr Phe Arg Pro Tyr Ile Tyr Ala Leu Leu Lys Asp Asp Ser Lys Ile
         35                  40                  45

Glu Glu Val Lys Lys Ile Thr Ala Glu Arg His Gly Lys Ile Val Arg
     50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                 85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190
```

```
Arg Phe Leu Lys Ile Ile Arg Glu Lys Asp Pro Asp Ile Ile Thr
            195                 200                 205
Tyr Asn Gly Asp Ser Phe Asp Leu Pro Tyr Leu Ala Lys Arg Ala Glu
        210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Thr Gly Glu Gly
290                 295                 300
Leu Glu Arg Val Ala Lys Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
370                 375                 380
Tyr Ala Gly Gly Phe Val Lys Glu Pro Glu Lys Gly Leu Trp Glu Asn
385                 390                 395                 400
Ile Val Ser Leu Asp Phe Arg Ala Leu Tyr Pro Ser Ile Ile Ile Thr
                405                 410                 415
His Asn Val Ser Pro Asp Thr Leu Asn Arg Glu Gly Cys Arg Asn Tyr
            420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Asp Glu Arg Gln Lys Ile
450                 455                 460
Lys Thr Lys Met Lys Ala Ser Gln Asp Pro Ile Glu Lys Ile Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Trp Lys Glu
        515                 520                 525
Leu Glu Glu Lys Phe Gly Phe Lys Val Leu Tyr Ile Asp Thr Asp Gly
530                 535                 540
Leu Tyr Ala Thr Ile Pro Gly Gly Lys Ser Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Lys Tyr Ala Leu Ile Asp Glu Glu Gly Lys Ile Ile Thr Arg Gly
        595                 600                 605
```

```
Leu Glu Ile Val Arg Arg Asp Trp Ser Glu Ile Ala Lys Glu Thr Gln
610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
        755                 760                 765

Trp Leu Asn Ile Lys Lys Ser Gly Thr Gly Gly Gly Gly Ala Thr Val
770                 775                 780

Lys Phe Lys Tyr Lys Gly Glu Glu Lys Glu Val Asp Ile Ser Lys Ile
785                 790                 795                 800

Lys Lys Val Trp Arg Val Gly Glu Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
        835                 840

<210> SEQ ID NO 41
<211> LENGTH: 844
<212> TYPE: PRT
<213> ORGANISM: Artificial Sequence
<220> FEATURE:
<223> OTHER INFORMATION: synthetic polymerase + linker + Sso7d-K28N
      polymerase conjugate

<400> SEQUENCE: 41

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125
```

```
Met Glu Gly Asp Glu Glu Leu Lys Leu Leu Ala Phe Ala Ile Ala Thr
130                 135                 140

Leu Tyr His Glu Gly Glu Phe Gly Lys Gly Pro Ile Ile Met Ile
145                 150                 155                 160

Ser Tyr Ala Asp Glu Glu Ala Lys Val Ile Thr Trp Lys Lys Ile
            165                 170                 175

Asp Leu Pro Tyr Val Glu Val Ser Ser Glu Arg Glu Met Ile Lys
                180                 185                 190

Arg Phe Leu Lys Ile Ile Arg Glu Lys Asp Pro Asp Ile Ile Ile Thr
            195                 200                 205

Tyr Asn Gly Asp Ser Phe Asp Leu Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Thr Gly Glu Gly
290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Lys Ile
450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
            515                 520                 525

Leu Glu Glu Lys Phe Gly Phe Lys Val Leu Tyr Ile Asp Thr Asp Gly
530                 535                 540
```

Leu Tyr Ala Thr Ile Pro Gly Gly Lys Ser Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Trp Gln Lys Thr Lys Gln Thr Gly Leu Thr Ser
            755                 760                 765

Trp Leu Asn Ile Lys Lys Ser Gly Thr Gly Gly Gly Ala Thr Val
        770                 775                 780

Lys Phe Lys Tyr Lys Gly Glu Glu Lys Glu Val Asp Ile Ser Lys Ile
785                 790                 795                 800

Lys Lys Val Trp Arg Val Gly Asn Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
        835                 840

<210> SEQ ID NO 42
<211> LENGTH: 844
<212> TYPE: PRT
<213> ORGANISM: Artificial Sequence
<220> FEATURE:
<223> OTHER INFORMATION: synthetic polymerase + linker + Sso7d-K28Q
    polymerase conjugate

<400> SEQUENCE: 42

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
                20                  25                  30

Thr Phe Arg Pro Tyr Ile Tyr Ala Leu Leu Lys Asp Asp Ser Lys Ile
            35                  40                  45

Glu Glu Val Lys Lys Ile Thr Ala Glu Arg His Gly Lys Ile Val Arg
        50                  55                  60

```
Ile Val Asp Ala Glu Lys Val Glu Lys Lys Phe Leu Gly Arg Pro Ile
 65                  70                  75                  80

Thr Val Trp Arg Leu Tyr Phe Glu His Pro Gln Asp Val Pro Thr Ile
                 85                  90                  95

Arg Glu Lys Ile Arg Glu His Ser Ala Val Asp Ile Phe Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Ala Ile Ala Thr
130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Ser Ser Glu Arg Glu Met Ile Lys
                180                 185                 190

Arg Phe Leu Lys Ile Ile Arg Glu Lys Asp Pro Asp Ile Ile Ile Thr
            195                 200                 205

Tyr Asn Gly Asp Ser Phe Asp Leu Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala Asp Glu Ile Ala Lys Ala Trp Glu Thr Gly Glu Gly
            290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Arg Glu Tyr Glu Arg Arg Leu Arg Glu Ser
            370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Thr
                405                 410                 415

His Asn Val Ser Pro Asp Thr Leu Asn Arg Glu Gly Cys Arg Asn Tyr
                420                 425                 430

Asp Val Ala Pro Glu Val Gly His Lys Phe Cys Lys Asp Phe Pro Gly
                435                 440                 445

Phe Ile Pro Ser Leu Leu Lys Arg Leu Leu Asp Glu Arg Gln Lys Ile
            450                 455                 460

Lys Thr Lys Met Lys Ala Ser Gln Asp Pro Ile Glu Lys Ile Met Leu
465                 470                 475                 480
```

Asp Tyr Arg Gln Arg Ala Ile Lys Ile Leu Ala Asn Ser Tyr Tyr Gly
            485                 490                 495

Tyr Tyr Gly Tyr Ala Lys Ala Arg Trp Tyr Cys Lys Glu Cys Ala Glu
        500                 505                 510

Ser Val Thr Ala Trp Gly Arg Glu Tyr Ile Glu Phe Val Trp Lys Glu
    515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Lys Ser Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
        755                 760                 765

Trp Leu Asn Ile Lys Lys Ser Gly Thr Gly Gly Gly Ala Thr Val
    770                 775                 780

Lys Phe Lys Tyr Lys Gly Glu Glu Lys Glu Val Asp Ile Ser Lys Ile
785                 790                 795                 800

Lys Lys Val Trp Arg Val Gly Gln Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
        835                 840

<210> SEQ ID NO 43
<211> LENGTH: 844
<212> TYPE: PRT
<213> ORGANISM: Artificial Sequence
<220> FEATURE:
<223> OTHER INFORMATION: synthetic polymerase + linker + Sso7d-R43G
      polymerase conjugate

<400> SEQUENCE: 43

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
            85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
            165                 170                 175

Asp Leu Pro Tyr Val Glu Val Ser Ser Glu Arg Glu Met Ile Lys
            180                 185                 190

Arg Phe Leu Lys Ile Ile Arg Glu Lys Asp Pro Asp Ile Ile Ile Thr
            195                 200                 205

Tyr Asn Gly Asp Ser Phe Asp Leu Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
        290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
            325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
        370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
            405                 410                 415

```
His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Lys Ile
            450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
                595                 600                 605

Leu Glu Ile Val Arg Arg Asp Trp Ser Glu Ile Ala Lys Glu Thr Gln
610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
            755                 760                 765

Trp Leu Asn Ile Lys Lys Ser Gly Thr Gly Gly Gly Gly Ala Thr Val
            770                 775                 780

Lys Phe Lys Tyr Lys Gly Glu Glu Lys Glu Val Asp Ile Ser Lys Ile
785                 790                 795                 800

Lys Lys Val Trp Arg Val Gly Ser Met Ile Ser Phe Thr Tyr Asp Glu
                805                 810                 815

Gly Gly Gly Lys Thr Gly Gly Gly Ala Val Ser Glu Lys Asp Ala Pro
            820                 825                 830

Lys Glu Leu Leu Gln Met Leu Glu Lys Gln Lys Lys
```

<210> SEQ ID NO 44
<211> LENGTH: 844
<212> TYPE: PRT
<213> ORGANISM: Artificial Sequence
<220> FEATURE:
<223> OTHER INFORMATION: synthetic polymerase + linker + Sso7d-R43A polymerase conjugate

<400> SEQUENCE: 44

```
Met Ile Leu Asp Ala Asp Tyr Ile Thr Glu Glu Gly Lys Pro Val Ile
 1               5                  10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Ile Ile Arg Glu Lys Asp Pro Asp Ile Ile Ile Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350
```

```
Val Glu Trp Phe Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
370                 375                 380
Tyr Ala Gly Gly Phe Val Lys Glu Pro Glu Lys Gly Leu Trp Glu Asn
385                 390                 395                 400
Ile Val Ser Leu Asp Phe Arg Ala Leu Tyr Pro Ser Ile Ile Ile Thr
                405                 410                 415
His Asn Val Ser Pro Asp Thr Leu Asn Arg Glu Gly Cys Arg Asn Tyr
            420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Asp Glu Arg Gln Lys Ile
    450                 455                 460
Lys Thr Lys Met Lys Ala Ser Gln Asp Pro Ile Glu Lys Ile Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Trp Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Lys Ser Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Lys Tyr Ala Leu Ile Asp Glu Glu Gly Lys Ile Ile Thr Arg Gly
        595                 600                 605
Leu Glu Ile Val Arg Arg Asp Trp Ser Glu Ile Ala Lys Glu Thr Gln
    610                 615                 620
Ala Arg Val Leu Glu Ala Ile Leu Lys His Gly Asn Val Glu Glu Ala
625                 630                 635                 640
Val Arg Ile Val Lys Glu Val Thr Gln Lys Leu Ser Lys Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Arg Leu Ala
        675                 680                 685
Ala Lys Gly Val Lys Ile Lys Pro Gly Met Val Ile Gly Tyr Ile Val
690                 695                 700
Leu Arg Gly Asp Gly Pro Ile Ser Asn Arg Ala Ile Leu Ala Glu Glu
705                 710                 715                 720
Tyr Asp Pro Arg Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Trp Gln Lys Thr Lys Gln Thr Gly Leu Thr Ser
        755                 760                 765
Trp Leu Asn Ile Lys Lys Ser Gly Thr Gly Gly Gly Gly Ala Thr Val
```

```
            770                 775                 780
Lys Phe Lys Tyr Lys Gly Glu Lys Glu Val Asp Ile Ser Lys Ile
785                 790                 795                 800

Lys Lys Val Trp Arg Val Gly Ser Met Ile Ser Phe Thr Tyr Asp Glu
                805                 810                 815

Gly Gly Gly Lys Thr Gly Ala Gly Ala Val Ser Glu Lys Asp Ala Pro
                820                 825                 830

Lys Glu Leu Leu Gln Met Leu Gly Lys Gln Lys Lys
                835                 840

<210> SEQ ID NO 45
<211> LENGTH: 844
<212> TYPE: PRT
<213> ORGANISM: Artificial Sequence
<220> FEATURE:
<223> OTHER INFORMATION: synthetic polymerase + linker + Sso7d-R43S
      polymerase conjugate

<400> SEQUENCE: 45

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Ile Ile Arg Glu Lys Asp Pro Asp Ile Ile Ile Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285
```

Lys Val Tyr Ala Asp Glu Ile Ala Lys Ala Trp Glu Thr Gly Gly
290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu

```
                705                 710                 715                 720
Tyr Asp Pro Arg Lys His Lys Tyr Asp Ala Glu Tyr Tyr Ile Glu Asn
                    725                 730                 735
Gln Val Leu Pro Ala Val Leu Arg Ile Leu Glu Gly Phe Gly Tyr Arg
                    740                 745                 750
Lys Glu Asp Leu Arg Trp Gln Lys Thr Lys Gln Thr Gly Leu Thr Ser
                    755                 760                 765
Trp Leu Asn Ile Lys Lys Ser Gly Thr Gly Gly Gly Ala Thr Val
                    770                 775                 780
Lys Phe Lys Tyr Lys Gly Glu Lys Glu Val Asp Ile Ser Lys Ile
785                 790                 795                 800
Lys Lys Val Trp Arg Val Gly Ser Met Ile Ser Phe Thr Tyr Asp Glu
                    805                 810                 815
Gly Gly Gly Lys Thr Gly Ser Gly Ala Val Ser Glu Lys Asp Ala Pro
                    820                 825                 830
Lys Glu Leu Leu Gln Met Leu Glu Lys Gln Lys Lys
                    835                 840

<210> SEQ ID NO 46
<211> LENGTH: 844
<212> TYPE: PRT
<213> ORGANISM: Artificial Sequence
<220> FEATURE:
<223> OTHER INFORMATION: synthetic polymerase + linker + Sso7d-R43T
      polymerase conjugate

<400> SEQUENCE: 46

Met Ile Leu Asp Ala Asp Tyr Ile Thr Glu Gly Lys Pro Val Ile
  1                 5                  10                  15
Arg Leu Phe Lys Lys Glu Asn Gly Glu Phe Lys Ile Glu His Asp Arg
                    20                  25                  30
Thr Phe Arg Pro Tyr Ile Tyr Ala Leu Leu Lys Asp Asp Ser Lys Ile
                    35                  40                  45
Glu Glu Val Lys Lys Ile Thr Ala Glu Arg His Gly Lys Ile Val Arg
        50                  55                  60
Ile Val Asp Ala Glu Lys Val Glu Lys Lys Phe Leu Gly Arg Pro Ile
65                  70                  75                  80
Thr Val Trp Arg Leu Tyr Phe Glu His Pro Gln Asp Val Pro Thr Ile
                    85                  90                  95
Arg Glu Lys Ile Arg Glu His Ser Ala Val Val Asp Ile Phe Glu Tyr
                    100                 105                 110
Asp Ile Pro Phe Ala Lys Arg Tyr Leu Ile Asp Lys Gly Leu Ile Pro
                    115                 120                 125
Met Glu Gly Asp Glu Glu Leu Lys Leu Leu Ala Phe Ala Ile Ala Thr
        130                 135                 140
Leu Tyr His Glu Gly Glu Glu Phe Gly Lys Gly Pro Ile Ile Met Ile
145                 150                 155                 160
Ser Tyr Ala Asp Glu Glu Ala Lys Val Ile Thr Trp Lys Lys Ile
                    165                 170                 175
Asp Leu Pro Tyr Val Glu Val Val Ser Ser Glu Arg Glu Met Ile Lys
                    180                 185                 190
Arg Phe Leu Lys Ile Ile Arg Glu Lys Asp Pro Asp Ile Ile Ile Thr
                    195                 200                 205
Tyr Asn Gly Asp Ser Phe Asp Leu Pro Tyr Leu Ala Lys Arg Ala Glu
        210                 215                 220
```

-continued

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
            325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
            405                 410                 415

His Asn Val Ser Pro Asp Thr Leu Asn Arg Glu Gly Cys Arg Asn Tyr
        420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
            485                 490                 495

Tyr Tyr Gly Tyr Ala Lys Ala Arg Trp Tyr Cys Lys Glu Cys Ala Glu
        500                 505                 510

Ser Val Thr Ala Trp Gly Arg Glu Tyr Ile Glu Phe Val Trp Lys Glu
    515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
            565                 570                 575

Glu Leu Glu Tyr Glu Gly Phe Tyr Lys Arg Gly Phe Phe Val Thr Lys
        580                 585                 590

Lys Lys Tyr Ala Leu Ile Asp Glu Glu Gly Lys Ile Ile Thr Arg Gly
    595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile

```
                    645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Arg Leu Ala
            675                 680                 685
Ala Lys Gly Val Lys Ile Lys Pro Gly Met Val Ile Gly Tyr Ile Val
            690                 695                 700
Leu Arg Gly Asp Gly Pro Ile Ser Asn Arg Ala Ile Leu Ala Glu Glu
705                 710                 715                 720
Tyr Asp Pro Arg Lys His Lys Tyr Asp Ala Glu Tyr Tyr Ile Glu Asn
            725                 730                 735
Gln Val Leu Pro Ala Val Leu Arg Ile Leu Glu Gly Phe Gly Tyr Arg
            740                 745                 750
Lys Glu Asp Leu Arg Trp Gln Lys Thr Lys Gln Thr Gly Leu Thr Ser
            755                 760                 765
Trp Leu Asn Ile Lys Lys Ser Gly Thr Gly Gly Gly Gly Ala Thr Val
            770                 775                 780
Lys Phe Lys Tyr Lys Gly Glu Glu Lys Glu Val Asp Ile Ser Lys Ile
785                 790                 795                 800
Lys Lys Val Trp Arg Val Gly Ser Met Ile Ser Phe Thr Tyr Asp Glu
            805                 810                 815
Gly Gly Gly Lys Thr Gly Thr Gly Ala Val Ser Glu Lys Asp Ala Pro
            820                 825                 830
Lys Glu Leu Leu Gln Met Leu Glu Lys Gln Lys Lys
            835                 840

<210> SEQ ID NO 47
<211> LENGTH: 844
<212> TYPE: PRT
<213> ORGANISM: Artificial Sequence
<220> FEATURE:
<223> OTHER INFORMATION: synthetic polymerase + linker + Sso7d-R43C
      polymerase conjugate

<400> SEQUENCE: 47

Met Ile Leu Asp Ala Asp Tyr Ile Thr Glu Glu Gly Lys Pro Val Ile
1               5                   10                  15
Arg Leu Phe Lys Lys Glu Asn Gly Glu Phe Lys Ile Glu His Asp Arg
            20                  25                  30
Thr Phe Arg Pro Tyr Ile Tyr Ala Leu Leu Lys Asp Asp Ser Lys Ile
        35                  40                  45
Glu Glu Val Lys Lys Ile Thr Ala Glu Arg His Gly Lys Ile Val Arg
    50                  55                  60
Ile Val Asp Ala Glu Lys Val Glu Lys Lys Phe Leu Gly Arg Pro Ile
65                  70                  75                  80
Thr Val Trp Arg Leu Tyr Phe Glu His Pro Gln Asp Val Pro Thr Ile
            85                  90                  95
Arg Glu Lys Ile Arg Glu His Ser Ala Val Val Asp Ile Phe Glu Tyr
            100                 105                 110
Asp Ile Pro Phe Ala Lys Arg Tyr Leu Ile Asp Lys Gly Leu Ile Pro
        115                 120                 125
Met Glu Gly Asp Glu Glu Leu Lys Leu Leu Ala Phe Ala Ile Ala Thr
    130                 135                 140
Leu Tyr His Glu Gly Glu Glu Phe Gly Lys Gly Pro Ile Ile Met Ile
145                 150                 155                 160
```

```
Ser Tyr Ala Asp Glu Glu Ala Lys Val Ile Thr Trp Lys Lys Ile
            165                 170                 175

Asp Leu Pro Tyr Val Glu Val Ser Ser Glu Arg Glu Met Ile Lys
        180                 185                 190

Arg Phe Leu Lys Ile Ile Arg Glu Lys Asp Pro Asp Ile Ile Thr
            195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
    370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
    435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Lys Ser Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
```

```
                      580                 585                 590
Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
        610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
        755                 760                 765

Trp Leu Asn Ile Lys Lys Ser Gly Thr Gly Gly Gly Ala Thr Val
770                 775                 780

Lys Phe Lys Tyr Lys Gly Glu Glu Lys Glu Val Asp Ile Ser Lys Ile
785                 790                 795                 800

Lys Lys Val Trp Arg Val Gly Ser Met Ile Ser Phe Thr Tyr Asp Glu
                805                 810                 815

Gly Gly Gly Lys Thr Gly Cys Gly Ala Val Ser Glu Lys Asp Ala Pro
            820                 825                 830

Lys Glu Leu Leu Gln Met Leu Glu Lys Gln Lys Lys
        835                 840

<210> SEQ ID NO 48
<211> LENGTH: 844
<212> TYPE: PRT
<213> ORGANISM: Artificial Sequence
<220> FEATURE:
<223> OTHER INFORMATION: synthetic polymerase + linker + Sso7d-R43V
      polymerase conjugate

<400> SEQUENCE: 48

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95
```

```
Arg Glu Lys Ile Arg Glu His Ser Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Ala Ile Ala Thr
        130                 135                 140

Leu Tyr His Glu Gly Glu Phe Gly Lys Gly Pro Ile Ile Met Ile
145                 150                 155                 160

Ser Tyr Ala Asp Glu Glu Ala Lys Val Ile Thr Trp Lys Lys Ile
                165                 170                 175

Asp Leu Pro Tyr Val Glu Val Ser Ser Glu Arg Glu Met Ile Lys
            180                 185                 190

Arg Phe Leu Lys Ile Ile Arg Glu Lys Asp Pro Asp Ile Ile Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
```

```
            515                 520                 525
Leu Glu Glu Lys Phe Gly Phe Lys Val Leu Tyr Ile Asp Thr Asp Gly
    530                 535                 540

Leu Tyr Ala Thr Ile Pro Gly Gly Lys Ser Glu Ile Lys Lys Lys
545                 550                 555                 560

Ala Leu Glu Phe Val Asp Tyr Ile Asn Ala Lys Leu Pro Gly Leu Leu
            565                 570                 575

Glu Leu Glu Tyr Glu Gly Phe Tyr Lys Arg Gly Phe Phe Val Thr Lys
        580                 585                 590

Lys Lys Tyr Ala Leu Ile Asp Glu Glu Gly Lys Ile Ile Thr Arg Gly
    595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
            645                 650                 655

Pro Pro Glu Lys Leu Ala Ile Tyr Glu Gln Ile Thr Arg Pro Leu His
        660                 665                 670

Glu Tyr Lys Ala Ile Gly Pro His Val Ala Val Ala Lys Arg Leu Ala
    675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
            725                 730                 735

Gln Val Leu Pro Ala Val Leu Arg Ile Leu Glu Gly Phe Gly Tyr Arg
        740                 745                 750

Lys Glu Asp Leu Arg Trp Gln Lys Thr Lys Gln Thr Gly Leu Thr Ser
    755                 760                 765

Trp Leu Asn Ile Lys Lys Ser Gly Thr Gly Gly Gly Ala Thr Val
    770                 775                 780

Lys Phe Lys Tyr Lys Gly Glu Glu Lys Glu Val Asp Ile Ser Lys Ile
785                 790                 795                 800

Lys Lys Val Trp Arg Val Gly Ser Met Ile Ser Phe Thr Tyr Asp Glu
            805                 810                 815

Gly Gly Gly Lys Thr Gly Val Gly Ala Val Ser Glu Lys Asp Ala Pro
        820                 825                 830

Lys Glu Leu Leu Gln Met Leu Glu Lys Gln Lys Lys
        835                 840

<210> SEQ ID NO 49
<211> LENGTH: 844
<212> TYPE: PRT
<213> ORGANISM: Artificial Sequence
<220> FEATURE:
<223> OTHER INFORMATION: synthetic polymerase + linker + Sso7d-R43L
      polymerase conjugate

<400> SEQUENCE: 49

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30
```

-continued

```
Thr Phe Arg Pro Tyr Ile Tyr Ala Leu Leu Lys Asp Ser Lys Ile
         35                  40                  45

Glu Glu Val Lys Lys Ile Thr Ala Glu Arg His Gly Lys Ile Val Arg
 50                  55                  60

Ile Val Asp Ala Glu Lys Val Glu Lys Phe Leu Gly Arg Pro Ile
 65                  70                  75                  80

Thr Val Trp Arg Leu Tyr Phe Glu His Pro Gln Asp Val Pro Thr Ile
                     85                  90                  95

Arg Glu Lys Ile Arg Glu His Ser Ala Val Val Asp Ile Phe Glu Tyr
                100                 105                 110

Asp Ile Pro Phe Ala Lys Arg Tyr Leu Ile Asp Lys Gly Leu Ile Pro
                115                 120                 125

Met Glu Gly Asp Glu Glu Leu Lys Leu Leu Ala Phe Ala Ile Ala Thr
        130                 135                 140

Leu Tyr His Glu Gly Glu Glu Phe Gly Lys Gly Pro Ile Ile Met Ile
145                 150                 155                 160

Ser Tyr Ala Asp Glu Glu Ala Lys Val Ile Thr Trp Lys Lys Ile
                165                 170                 175

Asp Leu Pro Tyr Val Glu Val Val Ser Ser Glu Arg Glu Met Ile Lys
                180                 185                 190

Arg Phe Leu Lys Ile Ile Arg Glu Lys Asp Pro Asp Ile Ile Ile Thr
        195                 200                 205

Tyr Asn Gly Asp Ser Phe Asp Leu Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
        340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
        370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
                420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
```

```
            450                 455                 460
Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Lys Ser Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
            755                 760                 765

Trp Leu Asn Ile Lys Lys Ser Gly Thr Gly Gly Gly Ala Thr Val
770                 775                 780

Lys Phe Lys Tyr Lys Gly Glu Glu Lys Glu Val Asp Ile Ser Lys Ile
785                 790                 795                 800

Lys Lys Val Trp Arg Val Gly Ser Met Ile Ser Phe Thr Tyr Asp Glu
            805                 810                 815

Gly Gly Gly Lys Thr Gly Leu Gly Ala Val Ser Glu Lys Asp Ala Pro
            820                 825                 830

Lys Glu Leu Leu Gln Met Leu Glu Lys Gln Lys Lys
            835                 840

<210> SEQ ID NO 50
<211> LENGTH: 844
<212> TYPE: PRT
<213> ORGANISM: Artificial Sequence
```

<220> FEATURE:
<223> OTHER INFORMATION: synthetic polymerase + linker + Sso7d-R43I
     polymerase conjugate

<400> SEQUENCE: 50

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Ala Ile Ala Thr
130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Ser Ser Glu Arg Glu Met Ile Lys
            180                 185                 190

Arg Phe Leu Lys Ile Ile Arg Glu Lys Asp Pro Asp Ile Ile Ile Thr
        195                 200                 205

Tyr Asn Gly Asp Ser Phe Asp Leu Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
370                 375                 380

Tyr Ala Gly Gly Phe Val Lys Glu Pro Glu Lys Gly Leu Trp Glu Asn

```
385                 390                 395                 400
Ile Val Ser Leu Asp Phe Arg Ala Leu Tyr Pro Ser Ile Ile Ile Thr
                405                 410                 415
His Asn Val Ser Pro Asp Thr Leu Asn Arg Glu Gly Cys Arg Asn Tyr
                420                 425                 430
Asp Val Ala Pro Glu Val Gly His Lys Phe Cys Lys Asp Phe Pro Gly
                435                 440                 445
Phe Ile Pro Ser Leu Leu Lys Arg Leu Leu Asp Glu Arg Gln Lys Ile
            450                 455                 460
Lys Thr Lys Met Lys Ala Ser Gln Asp Pro Ile Glu Lys Ile Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
                500                 505                 510
Ser Val Thr Ala Trp Gly Arg Glu Tyr Ile Glu Phe Val Trp Lys Glu
            515                 520                 525
Leu Glu Glu Lys Phe Gly Phe Lys Val Leu Tyr Ile Asp Thr Asp Gly
            530                 535                 540
Leu Tyr Ala Thr Ile Pro Gly Gly Lys Ser Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Lys Arg Gly Phe Phe Val Thr Lys
                580                 585                 590
Lys Lys Tyr Ala Leu Ile Asp Glu Glu Gly Lys Ile Ile Thr Arg Gly
            595                 600                 605
Leu Glu Ile Val Arg Arg Asp Trp Ser Glu Ile Ala Lys Glu Thr Gln
            610                 615                 620
Ala Arg Val Leu Glu Ala Ile Leu Lys His Gly Asn Val Glu Glu Ala
625                 630                 635                 640
Val Arg Ile Val Lys Glu Val Thr Gln Lys Leu Ser Lys Tyr Glu Ile
                645                 650                 655
Pro Pro Glu Lys Leu Ala Ile Tyr Glu Gln Ile Thr Arg Pro Leu His
                660                 665                 670
Glu Tyr Lys Ala Ile Gly Pro His Val Ala Val Ala Lys Arg Leu Ala
            675                 680                 685
Ala Lys Gly Val Lys Ile Lys Pro Gly Met Val Ile Gly Tyr Ile Val
            690                 695                 700
Leu Arg Gly Asp Gly Pro Ile Ser Asn Arg Ala Ile Leu Ala Glu Glu
705                 710                 715                 720
Tyr Asp Pro Arg Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
                740                 745                 750
Lys Glu Asp Leu Arg Trp Gln Lys Thr Lys Gln Thr Gly Leu Thr Ser
            755                 760                 765
Trp Leu Asn Ile Lys Lys Ser Gly Thr Gly Gly Gly Gly Ala Thr Val
            770                 775                 780
Lys Phe Lys Tyr Lys Gly Glu Glu Lys Glu Val Asp Ile Ser Lys Ile
785                 790                 795                 800
Lys Lys Val Trp Arg Val Gly Ser Met Ile Ser Phe Thr Tyr Asp Glu
                805                 810                 815
```

-continued

```
Gly Gly Gly Lys Thr Gly Ile Gly Ala Val Ser Glu Lys Asp Ala Pro
            820                 825                 830

Lys Glu Leu Gln Met Leu Glu Lys Gln Lys Lys
            835                 840
```

<210> SEQ ID NO 51
<211> LENGTH: 844
<212> TYPE: PRT
<213> ORGANISM: Artificial Sequence
<220> FEATURE:
<223> OTHER INFORMATION: synthetic polymerase + linker + Sso7d-R43M polymerase conjugate

<400> SEQUENCE: 51

```
Met Ile Leu Asp Ala Asp Tyr Ile Thr Glu Glu Gly Lys Pro Val Ile
 1               5                  10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Ser Ser Glu Arg Glu Met Ile Lys
            180                 185                 190

Arg Phe Leu Lys Ile Ile Arg Glu Lys Asp Pro Asp Ile Ile Ile Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
```

```
            325                 330                 335
Val Gly Gln Pro Leu Trp Asp Val Ser Arg Ser Thr Gly Asn Leu
        340                 345                 350
Val Glu Trp Phe Leu Leu Arg Lys Ala Tyr Glu Arg Asn Glu Leu Ala
355                 360                 365
Pro Asn Lys Pro Asp Glu Arg Glu Tyr Glu Arg Arg Leu Arg Glu Ser
        370                 375                 380
Tyr Ala Gly Gly Phe Val Lys Glu Pro Glu Lys Gly Leu Trp Glu Asn
385                 390                 395                 400
Ile Val Ser Leu Asp Phe Arg Ala Leu Tyr Pro Ser Ile Ile Thr
                405                 410                 415
His Asn Val Ser Pro Asp Thr Leu Asn Arg Glu Gly Cys Arg Asn Tyr
                420                 425                 430
Asp Val Ala Pro Glu Val Gly His Lys Phe Cys Lys Asp Phe Pro Gly
                435                 440                 445
Phe Ile Pro Ser Leu Leu Lys Arg Leu Leu Asp Glu Arg Gln Lys Ile
        450                 455                 460
Lys Thr Lys Met Lys Ala Ser Gln Asp Pro Ile Glu Lys Ile Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
                500                 505                 510
Ser Val Thr Ala Trp Gly Arg Glu Tyr Ile Glu Phe Val Trp Lys Glu
                515                 520                 525
Leu Glu Glu Lys Phe Gly Phe Lys Val Leu Tyr Ile Asp Thr Asp Gly
        530                 535                 540
Leu Tyr Ala Thr Ile Pro Gly Gly Lys Ser Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Lys Arg Gly Phe Phe Val Thr Lys
                580                 585                 590
Lys Lys Tyr Ala Leu Ile Asp Glu Glu Gly Lys Ile Ile Thr Arg Gly
                595                 600                 605
Leu Glu Ile Val Arg Arg Asp Trp Ser Glu Ile Ala Lys Glu Thr Gln
        610                 615                 620
Ala Arg Val Leu Glu Ala Ile Leu Lys His Gly Asn Val Glu Glu Ala
625                 630                 635                 640
Val Arg Ile Val Lys Glu Val Thr Gln Lys Leu Ser Lys Tyr Glu Ile
                645                 650                 655
Pro Pro Glu Lys Leu Ala Ile Tyr Glu Gln Ile Thr Arg Pro Leu His
                660                 665                 670
Glu Tyr Lys Ala Ile Gly Pro His Val Ala Val Ala Lys Arg Leu Ala
                675                 680                 685
Ala Lys Gly Val Lys Ile Lys Pro Gly Met Val Ile Gly Tyr Ile Val
        690                 695                 700
Leu Arg Gly Asp Gly Pro Ile Ser Asn Arg Ala Ile Leu Ala Glu Glu
705                 710                 715                 720
Tyr Asp Pro Arg Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
                740                 745                 750
```

```
Lys Glu Asp Leu Arg Trp Gln Lys Thr Lys Gln Thr Gly Leu Thr Ser
            755                 760                 765
Trp Leu Asn Ile Lys Lys Ser Gly Thr Gly Gly Gly Ala Thr Val
770             775                 780
Lys Phe Lys Tyr Lys Gly Glu Glu Lys Glu Val Asp Ile Ser Lys Ile
785                 790                 795                 800
Lys Lys Val Trp Arg Val Gly Ser Met Ile Ser Phe Thr Tyr Asp Glu
                805                 810                 815
Gly Gly Gly Lys Thr Gly Met Gly Ala Val Ser Glu Lys Asp Ala Pro
                820                 825                 830
Lys Glu Leu Leu Gln Met Leu Glu Lys Gln Lys Lys
                835                 840
```

<210> SEQ ID NO 52
<211> LENGTH: 844
<212> TYPE: PRT
<213> ORGANISM: Artificial Sequence
<220> FEATURE:
<223> OTHER INFORMATION: synthetic polymerase + linker + Sso7d-R43F
      polymerase conjugate

<400> SEQUENCE: 52

```
Met Ile Leu Asp Ala Asp Tyr Ile Thr Glu Glu Gly Lys Pro Val Ile
1               5                   10                  15
Arg Leu Phe Lys Lys Glu Asn Gly Glu Phe Lys Ile Glu His Asp Arg
                20                  25                  30
Thr Phe Arg Pro Tyr Ile Tyr Ala Leu Leu Lys Asp Asp Ser Lys Ile
                35                  40                  45
Glu Glu Val Lys Lys Ile Thr Ala Glu Arg His Gly Lys Ile Val Arg
            50                  55                  60
Ile Val Asp Ala Glu Lys Val Glu Lys Lys Phe Leu Gly Arg Pro Ile
65              70                  75                  80
Thr Val Trp Arg Leu Tyr Phe Glu His Pro Gln Asp Val Pro Thr Ile
                85                  90                  95
Arg Glu Lys Ile Arg Glu His Ser Ala Val Val Asp Ile Phe Glu Tyr
                100                 105                 110
Asp Ile Pro Phe Ala Lys Arg Tyr Leu Ile Asp Lys Gly Leu Ile Pro
                115                 120                 125
Met Glu Gly Asp Glu Glu Leu Lys Leu Leu Ala Phe Ala Ile Ala Thr
                130                 135                 140
Leu Tyr His Glu Gly Glu Glu Phe Gly Lys Gly Pro Ile Ile Met Ile
145                 150                 155                 160
Ser Tyr Ala Asp Glu Glu Glu Ala Lys Val Ile Thr Trp Lys Lys Ile
                165                 170                 175
Asp Leu Pro Tyr Val Glu Val Val Ser Ser Glu Arg Glu Met Ile Lys
                180                 185                 190
Arg Phe Leu Lys Ile Ile Arg Glu Lys Asp Pro Asp Ile Ile Ile Thr
                195                 200                 205
Tyr Asn Gly Asp Ser Phe Asp Leu Pro Tyr Leu Ala Lys Arg Ala Glu
            210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Arg Arg Thr Ile Asn Leu Pro Thr
```

```
            260                 265                 270
Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Thr Gly Glu Gly
            290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                    325                 330                 335

Val Gly Gln Pro Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
            370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                    405                 410                 415

His Asn Val Ser Pro Asp Thr Leu Asn Arg Glu Gly Cys Arg Asn Tyr
                    420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Lys Ile
            450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                    485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Glu Tyr Ile Glu Phe Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                    565                 570                 575

Glu Leu Glu Tyr Glu Gly Phe Tyr Lys Arg Gly Phe Phe Val Thr Lys
                    580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                    645                 650                 655

Pro Pro Glu Lys Leu Ala Ile Tyr Glu Gln Ile Thr Arg Pro Leu His
                    660                 665                 670

Glu Tyr Lys Ala Ile Gly Pro His Val Ala Val Ala Lys Arg Leu Ala
            675                 680                 685
```

```
Ala Lys Gly Val Lys Ile Lys Pro Gly Met Val Ile Gly Tyr Ile Val
        690                 695                 700
Leu Arg Gly Asp Gly Pro Ile Ser Asn Arg Ala Ile Leu Ala Glu Glu
705                 710                 715                 720
Tyr Asp Pro Arg Lys His Lys Tyr Asp Ala Glu Tyr Tyr Ile Glu Asn
                    725                 730                 735
Gln Val Leu Pro Ala Val Leu Arg Ile Leu Glu Gly Phe Gly Tyr Arg
            740                 745                 750
Lys Glu Asp Leu Arg Trp Gln Lys Thr Lys Gln Thr Gly Leu Thr Ser
        755                 760                 765
Trp Leu Asn Ile Lys Lys Ser Gly Thr Gly Gly Gly Ala Thr Val
770                 775                 780
Lys Phe Lys Tyr Lys Gly Glu Glu Lys Glu Val Asp Ile Ser Lys Ile
785                 790                 795                 800
Lys Lys Val Trp Arg Val Gly Ser Met Ile Ser Phe Thr Tyr Asp Glu
                    805                 810                 815
Gly Gly Gly Lys Thr Gly Phe Gly Ala Val Ser Glu Lys Asp Ala Pro
            820                 825                 830
Lys Glu Leu Leu Gln Met Leu Glu Lys Gln Lys Lys
        835                 840
```

<210> SEQ ID NO 53
<211> LENGTH: 844
<212> TYPE: PRT
<213> ORGANISM: Artificial Sequence
<220> FEATURE:
<223> OTHER INFORMATION: synthetic polymerase + linker + Sso7d-R43Y
    polymerase conjugate

<400> SEQUENCE: 53

```
Met Ile Leu Asp Ala Asp Tyr Ile Thr Glu Glu Gly Lys Pro Val Ile
1               5                   10                  15
Arg Leu Phe Lys Lys Glu Asn Gly Glu Phe Lys Ile Glu His Asp Arg
            20                  25                  30
Thr Phe Arg Pro Tyr Ile Tyr Ala Leu Leu Lys Asp Asp Ser Lys Ile
        35                  40                  45
Glu Glu Val Lys Lys Ile Thr Ala Glu Arg His Gly Lys Ile Val Arg
50                  55                  60
Ile Val Asp Ala Glu Lys Val Glu Lys Lys Phe Leu Gly Arg Pro Ile
65                  70                  75                  80
Thr Val Trp Arg Leu Tyr Phe Glu His Pro Gln Asp Val Pro Thr Ile
                    85                  90                  95
Arg Glu Lys Ile Arg Glu His Ser Ala Val Val Asp Ile Phe Glu Tyr
            100                 105                 110
Asp Ile Pro Phe Ala Lys Arg Tyr Leu Ile Asp Lys Gly Leu Ile Pro
        115                 120                 125
Met Glu Gly Asp Glu Glu Leu Lys Leu Leu Ala Phe Ala Ile Ala Thr
130                 135                 140
Leu Tyr His Glu Gly Glu Glu Phe Gly Lys Gly Pro Ile Ile Met Ile
145                 150                 155                 160
Ser Tyr Ala Asp Glu Glu Glu Ala Lys Val Ile Thr Trp Lys Lys Ile
                    165                 170                 175
Asp Leu Pro Tyr Val Glu Val Val Ser Ser Glu Arg Glu Met Ile Lys
            180                 185                 190
Arg Phe Leu Lys Ile Ile Arg Glu Lys Asp Pro Asp Ile Ile Ile Thr
```

```
                195                 200                 205
Tyr Asn Gly Asp Ser Phe Asp Leu Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Thr Gly Glu Gly
    290                 295                 300
Leu Glu Arg Val Ala Lys Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Pro Leu Trp Asp Val Ser Arg Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
    370                 375                 380
Tyr Ala Gly Gly Phe Val Lys Glu Pro Glu Lys Gly Leu Trp Glu Asn
385                 390                 395                 400
Ile Val Ser Leu Asp Phe Arg Ala Leu Tyr Pro Ser Ile Ile Ile Thr
                405                 410                 415
His Asn Val Ser Pro Asp Thr Leu Asn Arg Glu Gly Cys Arg Asn Tyr
            420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Asp Glu Arg Gln Lys Ile
    450                 455                 460
Lys Thr Lys Met Lys Ala Ser Gln Asp Pro Ile Glu Lys Ile Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Trp Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Lys Ser Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Lys Tyr Ala Leu Ile Asp Glu Glu Gly Lys Ile Ile Thr Arg Gly
        595                 600                 605
Leu Glu Ile Val Arg Arg Asp Trp Ser Glu Ile Ala Lys Glu Thr Gln
    610                 615                 620
```

```
Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
            645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
            725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
            755                 760                 765

Trp Leu Asn Ile Lys Lys Ser Gly Thr Gly Gly Gly Ala Thr Val
            770                 775                 780

Lys Phe Lys Tyr Lys Gly Glu Glu Lys Glu Val Asp Ile Ser Lys Ile
785                 790                 795                 800

Lys Lys Val Trp Arg Val Gly Ser Met Ile Ser Phe Thr Tyr Asp Glu
            805                 810                 815

Gly Gly Gly Lys Thr Gly Tyr Gly Ala Val Ser Glu Lys Asp Ala Pro
            820                 825                 830

Lys Glu Leu Leu Gln Met Leu Glu Lys Gln Lys Lys
            835                 840

<210> SEQ ID NO 54
<211> LENGTH: 844
<212> TYPE: PRT
<213> ORGANISM: Artificial Sequence
<220> FEATURE:
<223> OTHER INFORMATION: synthetic polymerase + linker + Sso7d-R43W
      polymerase conjugate

<400> SEQUENCE: 54

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
            35                  40                  45

Glu Glu Val Lys Lys Ile Thr Ala Glu Arg His Gly Lys Ile Val Arg
50                  55                  60

Ile Val Asp Ala Glu Lys Val Lys Lys Phe Leu Gly Arg Pro Ile
65                  70                  75                  80

Thr Val Trp Arg Leu Tyr Phe Glu His Pro Gln Asp Val Pro Thr Ile
            85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Ala Ile Ala Thr
```

```
                130                 135                 140
Leu Tyr His Glu Gly Glu Phe Gly Lys Gly Pro Ile Ile Met Ile
145                 150                 155                 160

Ser Tyr Ala Asp Glu Glu Ala Lys Val Ile Thr Trp Lys Lys Ile
                165                 170                 175

Asp Leu Pro Tyr Val Glu Val Val Ser Ser Arg Glu Met Ile Lys
                180                 185                 190

Arg Phe Leu Lys Ile Ile Arg Glu Lys Asp Pro Asp Ile Ile Thr
            195                 200                 205

Tyr Asn Gly Asp Ser Phe Asp Leu Pro Tyr Leu Ala Lys Arg Ala Glu
        210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Thr Gly Glu Gly
        290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Lys Ser Glu Glu Ile Lys Lys Lys
545                 550                 555                 560
```

Ala Leu Glu Phe Val Asp Tyr Ile Asn Ala Lys Leu Pro Gly Leu Leu
            565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
            645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
            725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
            755                 760                 765

Trp Leu Asn Ile Lys Lys Ser Gly Thr Gly Gly Gly Ala Thr Val
            770                 775                 780

Lys Phe Lys Tyr Lys Gly Glu Glu Lys Glu Val Asp Ile Ser Lys Ile
785                 790                 795                 800

Lys Lys Val Trp Arg Val Gly Ser Met Ile Ser Phe Thr Tyr Asp Glu
            805                 810                 815

Gly Gly Gly Lys Thr Gly Trp Gly Ala Val Ser Glu Lys Asp Ala Pro
            820                 825                 830

Lys Glu Leu Leu Gln Met Leu Glu Lys Gln Lys Lys
            835                 840

<210> SEQ ID NO 55
<211> LENGTH: 844
<212> TYPE: PRT
<213> ORGANISM: Artificial Sequence
<220> FEATURE:
<223> OTHER INFORMATION: synthetic polymerase + linker + Sso7d-R43D
      polymerase conjugate

<400> SEQUENCE: 55

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
            35                  40                  45

Glu Glu Val Lys Lys Ile Thr Ala Glu Arg His Gly Lys Ile Val Arg
        50                  55                  60

Ile Val Asp Ala Glu Lys Val Glu Lys Lys Phe Leu Gly Arg Pro Ile

```
            65                   70                   75                   80
Thr Val Trp Arg Leu Tyr Phe Glu His Pro Gln Asp Val Pro Thr Ile
                    85                   90                   95
Arg Glu Lys Ile Arg Glu His Ser Ala Val Val Asp Ile Phe Glu Tyr
                100                  105                  110
Asp Ile Pro Phe Ala Lys Arg Tyr Leu Ile Asp Lys Gly Leu Ile Pro
                115                  120                  125
Met Glu Gly Asp Glu Glu Leu Lys Leu Leu Ala Phe Ala Ile Ala Thr
            130                  135                  140
Leu Tyr His Glu Gly Glu Glu Phe Gly Lys Gly Pro Ile Ile Met Ile
145                  150                  155                  160
Ser Tyr Ala Asp Glu Glu Glu Ala Lys Val Ile Thr Trp Lys Lys Ile
                165                  170                  175
Asp Leu Pro Tyr Val Glu Val Val Ser Ser Glu Arg Glu Met Ile Lys
                180                  185                  190
Arg Phe Leu Lys Ile Ile Arg Glu Lys Asp Pro Asp Ile Ile Ile Thr
                195                  200                  205
Tyr Asn Gly Asp Ser Phe Asp Leu Pro Tyr Leu Ala Lys Arg Ala Glu
            210                  215                  220
Lys Leu Gly Ile Lys Leu Thr Ile Gly Arg Asp Gly Ser Glu Pro Lys
225                  230                  235                  240
Met Gln Arg Ile Gly Asp Met Thr Ala Val Glu Val Lys Gly Arg Ile
                245                  250                  255
His Phe Asp Leu Tyr His Val Ile Arg Arg Thr Ile Asn Leu Pro Thr
                260                  265                  270
Tyr Thr Leu Glu Ala Val Tyr Glu Ala Ile Phe Gly Lys Pro Lys Glu
            275                  280                  285
Lys Val Tyr Ala Asp Glu Ile Ala Lys Ala Trp Glu Thr Gly Glu Gly
            290                  295                  300
Leu Glu Arg Val Ala Lys Tyr Ser Met Glu Asp Ala Lys Ala Thr Tyr
305                  310                  315                  320
Glu Leu Gly Lys Glu Phe Phe Pro Met Glu Ala Gln Leu Ser Arg Leu
                325                  330                  335
Val Gly Gln Pro Leu Trp Asp Val Ser Arg Ser Ser Thr Gly Asn Leu
                340                  345                  350
Val Glu Trp Phe Leu Leu Arg Lys Ala Tyr Glu Arg Asn Glu Leu Ala
                355                  360                  365
Pro Asn Lys Pro Asp Glu Arg Glu Tyr Glu Arg Arg Leu Arg Glu Ser
            370                  375                  380
Tyr Ala Gly Gly Phe Val Lys Glu Pro Glu Lys Gly Leu Trp Glu Asn
385                  390                  395                  400
Ile Val Ser Leu Asp Phe Arg Ala Leu Tyr Pro Ser Ile Ile Ile Thr
                405                  410                  415
His Asn Val Ser Pro Asp Thr Leu Asn Arg Glu Gly Cys Arg Asn Tyr
                420                  425                  430
Asp Val Ala Pro Glu Val Gly His Lys Phe Cys Lys Asp Phe Pro Gly
            435                  440                  445
Phe Ile Pro Ser Leu Leu Lys Arg Leu Leu Asp Glu Arg Gln Lys Ile
            450                  455                  460
Lys Thr Lys Met Lys Ala Ser Gln Asp Pro Ile Glu Lys Ile Met Leu
465                  470                  475                  480
Asp Tyr Arg Gln Arg Ala Ile Lys Ile Leu Ala Asn Ser Tyr Tyr Gly
                485                  490                  495
```

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
        755                 760                 765

Trp Leu Asn Ile Lys Lys Ser Gly Thr Gly Gly Gly Gly Ala Thr Val
770                 775                 780

Lys Phe Lys Tyr Lys Gly Glu Glu Lys Glu Val Asp Ile Ser Lys Ile
785                 790                 795                 800

Lys Lys Val Trp Arg Val Gly Ser Met Ile Ser Phe Thr Tyr Asp Glu
                805                 810                 815

Gly Gly Gly Lys Thr Gly Asp Gly Ala Val Ser Glu Lys Asp Ala Pro
            820                 825                 830

Lys Glu Leu Leu Gln Met Leu Glu Lys Gln Lys Lys
        835                 840

<210> SEQ ID NO 56
<211> LENGTH: 844
<212> TYPE: PRT
<213> ORGANISM: Artificial Sequence
<220> FEATURE:
<223> OTHER INFORMATION: synthetic polymerase + linker + Sso7d-R43E
     polymerase conjugate

<400> SEQUENCE: 56

Met Ile Leu Asp Ala Asp Tyr Ile Thr Glu Glu Gly Lys Pro Val Ile

```
              1               5              10              15
            Arg Leu Phe Lys Lys Glu Asn Gly Glu Phe Lys Ile Glu His Asp Arg
                             20                  25                  30

Thr Phe Arg Pro Tyr Ile Tyr Ala Leu Leu Lys Asp Asp Ser Lys Ile
                             35                  40                  45

Glu Glu Val Lys Lys Ile Thr Ala Glu Arg His Gly Lys Ile Val Arg
                             50                  55                  60

Ile Val Asp Ala Glu Lys Val Glu Lys Lys Phe Leu Gly Arg Pro Ile
             65                  70                  75                  80

Thr Val Trp Arg Leu Tyr Phe Glu His Pro Gln Asp Val Pro Thr Ile
                             85                  90                  95

Arg Glu Lys Ile Arg Glu His Ser Ala Val Val Asp Ile Phe Glu Tyr
                            100                 105                 110

Asp Ile Pro Phe Ala Lys Arg Tyr Leu Ile Asp Lys Gly Leu Ile Pro
                            115                 120                 125

Met Glu Gly Asp Glu Glu Leu Lys Leu Leu Ala Phe Ala Ile Ala Thr
                            130                 135                 140

Leu Tyr His Glu Gly Glu Glu Phe Gly Lys Gly Pro Ile Ile Met Ile
            145                 150                 155                 160

Ser Tyr Ala Asp Glu Glu Ala Lys Val Ile Thr Trp Lys Lys Ile
                            165                 170                 175

Asp Leu Pro Tyr Val Glu Val Ser Ser Glu Arg Glu Met Ile Lys
                            180                 185                 190

Arg Phe Leu Lys Ile Ile Arg Glu Lys Asp Pro Asp Ile Ile Thr
                            195                 200                 205

Tyr Asn Gly Asp Ser Phe Asp Leu Pro Tyr Leu Ala Lys Arg Ala Glu
                            210                 215                 220

Lys Leu Gly Ile Lys Leu Thr Ile Gly Arg Asp Gly Ser Glu Pro Lys
            225                 230                 235                 240

Met Gln Arg Ile Gly Asp Met Thr Ala Val Glu Val Lys Gly Arg Ile
                            245                 250                 255

His Phe Asp Leu Tyr His Val Ile Arg Arg Thr Ile Asn Leu Pro Thr
                            260                 265                 270

Tyr Thr Leu Glu Ala Val Tyr Glu Ala Ile Phe Gly Lys Pro Lys Glu
                            275                 280                 285

Lys Val Tyr Ala Asp Glu Ile Ala Lys Ala Trp Glu Thr Gly Glu Gly
                            290                 295                 300

Leu Glu Arg Val Ala Lys Tyr Ser Met Glu Asp Ala Lys Ala Thr Tyr
            305                 310                 315                 320

Glu Leu Gly Lys Glu Phe Phe Pro Met Glu Ala Gln Leu Ser Arg Leu
                            325                 330                 335

Val Gly Gln Pro Leu Trp Asp Val Ser Arg Ser Ser Thr Gly Asn Leu
                            340                 345                 350

Val Glu Trp Phe Leu Leu Arg Lys Ala Tyr Glu Arg Asn Glu Leu Ala
                            355                 360                 365

Pro Asn Lys Pro Asp Glu Arg Glu Tyr Glu Arg Arg Leu Arg Glu Ser
                            370                 375                 380

Tyr Ala Gly Gly Phe Val Lys Glu Pro Glu Lys Gly Leu Trp Glu Asn
            385                 390                 395                 400

Ile Val Ser Leu Asp Phe Arg Ala Leu Tyr Pro Ser Ile Ile Ile Thr
                            405                 410                 415

His Asn Val Ser Pro Asp Thr Leu Asn Arg Glu Gly Cys Arg Asn Tyr
                            420                 425                 430
```

```
Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Lys Ile
        450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
            485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
            565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
        610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
            645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
            725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
        755                 760                 765

Trp Leu Asn Ile Lys Lys Ser Gly Thr Gly Gly Gly Gly Ala Thr Val
        770                 775                 780

Lys Phe Lys Tyr Lys Gly Glu Glu Lys Glu Val Asp Ile Ser Lys Ile
785                 790                 795                 800

Lys Lys Val Trp Arg Val Gly Ser Met Ile Ser Phe Thr Tyr Asp Glu
            805                 810                 815

Gly Gly Gly Lys Thr Gly Glu Gly Ala Val Ser Glu Lys Asp Ala Pro
            820                 825                 830

Lys Glu Leu Leu Gln Met Leu Glu Lys Gln Lys Lys
        835                 840
```

-continued

<210> SEQ ID NO 57
<211> LENGTH: 844
<212> TYPE: PRT
<213> ORGANISM: Artificial Sequence
<220> FEATURE:
<223> OTHER INFORMATION: synthetic polymerase + linker + Sso7d-R43N
      polymerase conjugate

<400> SEQUENCE: 57

```
Met Ile Leu Asp Ala Asp Tyr Ile Thr Glu Glu Gly Lys Pro Val Ile
 1               5                  10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Ser Ser Glu Arg Glu Met Ile Lys
            180                 185                 190

Arg Phe Leu Lys Ile Ile Arg Glu Lys Asp Pro Asp Ile Ile Ile Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365
```

```
Pro Asn Lys Pro Asp Glu Arg Glu Tyr Glu Arg Arg Leu Arg Glu Ser
        370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
        755                 760                 765

Trp Leu Asn Ile Lys Lys Ser Gly Thr Gly Gly Gly Gly Ala Thr Val
    770                 775                 780
```

```
Lys Phe Lys Tyr Lys Gly Glu Glu Lys Glu Val Asp Ile Ser Lys Ile
785                 790                 795                 800

Lys Lys Val Trp Arg Val Gly Ser Met Ile Ser Phe Thr Tyr Asp Glu
            805                 810                 815

Gly Gly Gly Lys Thr Gly Asn Gly Ala Val Ser Glu Lys Asp Ala Pro
        820                 825                 830

Lys Glu Leu Leu Gln Met Leu Glu Lys Gln Lys Lys
        835                 840

<210> SEQ ID NO 58
<211> LENGTH: 843
<212> TYPE: PRT
<213> ORGANISM: Artificial Sequence
<220> FEATURE:
<223> OTHER INFORMATION: synthetic polymerase + linker + Sso7d-R43Q
      polymerase conjugate

<400> SEQUENCE: 58

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Ala Ile Ala Thr
130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Ile Ile Arg Glu Lys Asp Pro Asp Ile Ile Ile Thr
        195                 200                 205

Tyr Asn Gly Asp Ser Phe Asp Leu Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
290                 295                 300
```

-continued

```
Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
            325                 330                 335

Val Gly Gln Pro Leu Trp Asp Val Ser Arg Ser Thr Gly Asn Leu
        340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
        370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
            485                 490                 495

Tyr Tyr Gly Tyr Ala Lys Ala Arg Trp Tyr Cys Lys Glu Cys Ala Glu
        500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720
```

```
Tyr Asp Pro Arg Lys His Lys Tyr Asp Ala Glu Tyr Tyr Ile Glu Asn
                    725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
        755                 760                 765

Trp Leu Asn Ile Lys Lys Ser Gly Thr Gly Gly Gly Gly Ala Thr Val
    770                 775                 780

Lys Phe Lys Tyr Lys Gly Glu Glu Lys Glu Val Asp Ile Ser Lys Ile
785                 790                 795                 800

Lys Lys Val Trp Arg Val Gly Ser Met Ile Ser Phe Thr Tyr Asp Glu
                805                 810                 815

Gly Gly Gly Lys Thr Gly Gln Gly Ala Val Ser Glu Lys Asp Ala Pro
            820                 825                 830

Lys Glu Leu Leu Gln Met Leu Glu Lys Gln Lys
        835                 840
```

<210> SEQ ID NO 59
<211> LENGTH: 844
<212> TYPE: PRT
<213> ORGANISM: Artificial Sequence
<220> FEATURE:
<223> OTHER INFORMATION: synthetic polymerase + linker + Sso7d-R43H polymerase conjugate

<400> SEQUENCE: 59

```
Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Ile Ile Arg Glu Lys Asp Pro Asp Ile Ile Ile Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240
```

-continued

```
Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655
```

```
Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
        755                 760                 765

Trp Leu Asn Ile Lys Lys Ser Gly Thr Gly Gly Gly Ala Thr Val
        770                 775                 780

Lys Phe Lys Tyr Lys Gly Glu Glu Lys Glu Val Asp Ile Ser Lys Ile
785                 790                 795                 800

Lys Lys Val Trp Arg Val Gly Ser Met Ile Ser Phe Thr Tyr Asp Glu
                805                 810                 815

Gly Gly Gly Lys Thr Gly His Gly Ala Val Ser Glu Lys Asp Ala Pro
            820                 825                 830

Lys Glu Leu Leu Gln Met Leu Glu Lys Gln Lys Lys
        835                 840

<210> SEQ ID NO 60
<211> LENGTH: 844
<212> TYPE: PRT
<213> ORGANISM: Artificial Sequence
<220> FEATURE:
<223> OTHER INFORMATION: synthetic polymerase + linker + Sso7d-R43K
      polymerase conjugate

<400> SEQUENCE: 60

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
                20                  25                  30

Thr Phe Arg Pro Tyr Ile Tyr Ala Leu Leu Lys Asp Asp Ser Lys Ile
            35                  40                  45

Glu Glu Val Lys Lys Ile Thr Ala Glu Arg His Gly Lys Ile Val Arg
        50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175
```

```
Asp Leu Pro Tyr Val Glu Val Ser Ser Glu Arg Glu Met Ile Lys
            180                 185                 190

Arg Phe Leu Lys Ile Ile Arg Glu Lys Asp Pro Asp Ile Ile Thr
            195                 200                 205

Tyr Asn Gly Asp Ser Phe Asp Leu Pro Tyr Leu Ala Lys Arg Ala Glu
            210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Thr Gly Glu Gly
            290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
            325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
            370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
            405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Lys Ile
450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
            485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
            565                 570                 575

Glu Leu Glu Tyr Glu Gly Phe Tyr Lys Arg Gly Phe Phe Val Thr Lys
            580                 585                 590
```

```
Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
        610                 615                 620

Ala Arg Val Leu Glu Ala Ile Leu Lys His Gly Asn Val Glu Ala
625                 630                 635                 640

Val Arg Ile Val Lys Glu Val Thr Gln Lys Leu Ser Lys Tyr Glu Ile
            645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
            725                 730                 735

Gln Val Leu Pro Ala Val Leu Arg Ile Leu Glu Gly Phe Gly Tyr Arg
        740                 745                 750

Lys Glu Asp Leu Arg Trp Gln Lys Thr Lys Gln Thr Gly Leu Thr Ser
        755                 760                 765

Trp Leu Asn Ile Lys Lys Ser Gly Thr Gly Gly Gly Ala Thr Val
        770                 775                 780

Lys Phe Lys Tyr Lys Gly Glu Glu Lys Glu Val Asp Ile Ser Lys Ile
785                 790                 795                 800

Lys Lys Val Trp Arg Val Gly Ser Met Ile Ser Phe Thr Tyr Asp Glu
            805                 810                 815

Gly Gly Gly Lys Thr Gly Lys Gly Ala Val Ser Glu Lys Asp Ala Pro
            820                 825                 830

Lys Glu Leu Leu Gln Met Leu Glu Lys Gln Lys Lys
            835                 840

<210> SEQ ID NO 61
<211> LENGTH: 775
<212> TYPE: PRT
<213> ORGANISM: Artificial Sequence
<220> FEATURE:
<223> OTHER INFORMATION: synthetic hybrid polymerase, polymerase
      conjugate

<400> SEQUENCE: 61

Met Ile Leu Asp Ala Asp Tyr Ile Thr Glu Glu Gly Lys Pro Val Ile
1               5                  10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Asp Glu Val Arg Lys Ile Thr Gly Glu Arg His Gly Lys Ile Val Arg
    50                  55                  60

Ile Val Asp Ala Glu Lys Val Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Asp Lys Val Arg Glu His Pro Ala Val Val Asp Ile Phe Glu Tyr
            100                 105                 110
```

```
Asp Ile Pro Phe Ala Lys Arg Tyr Leu Ile Asp Lys Gly Leu Ile Pro
            115                 120                 125
Met Glu Gly Glu Glu Leu Lys Ile Leu Ala Phe Asp Ile Glu Thr
    130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Val Ser Ser Glu Arg Glu Met Ile Lys
            180                 185                 190
Arg Phe Leu Arg Val Ile Arg Glu Lys Asp Pro Asp Val Ile Ile Thr
            195                 200                 205
Tyr Asn Gly Asp Ser Phe Asp Phe Pro Tyr Leu Val Lys Arg Ala Glu
        210                 215                 220
Lys Leu Gly Ile Lys Leu Thr Ile Gly Arg Asp Gly Ser Glu Pro Lys
225                 230                 235                 240
Met Gln Arg Leu Gly Asp Met Thr Ala Val Glu Ile Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Glu Ala Trp Glu Ser Gly Glu Gly
        290                 295                 300
Leu Glu Arg Val Ala Lys Tyr Ser Met Glu Asp Ala Lys Val Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Tyr Glu Arg Arg Leu Arg Glu Ser
        370                 375                 380
Tyr Ala Gly Gly Tyr Val Lys Glu Pro Glu Lys Gly Leu Trp Glu Asn
385                 390                 395                 400
Ile Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
            420                 425                 430
Asp Ile Ala Pro Glu Val Gly His Lys Phe Cys Lys Asp Phe Pro Gly
        435                 440                 445
Phe Ile Pro Ser Leu Leu Lys His Leu Leu Glu Glu Arg Gln Lys Ile
        450                 455                 460
Lys Thr Lys Met Lys Glu Ser Gln Asp Pro Ile Glu Lys Lys Met Leu
465                 470                 475                 480
Asp Tyr Arg Gln Arg Ala Ile Lys Ile Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Phe Val Trp Lys Glu
            515                 520                 525
```

-continued

Leu Glu Glu Lys Phe Gly Phe Lys Val Leu Tyr Ile Asp Thr Asp Gly
    530                 535                 540

Leu Tyr Ala Thr Ile Pro Gly Glu Pro Glu Glu Ile Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Arg Tyr Ala Val Ile Asp Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asn Val Glu Glu Ala
625                 630                 635                 640

Val Lys Ile Val Lys Glu Val Thr Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Arg Gly Val Lys Ile Lys Pro Gly Met Val Ile Gly Tyr Ile Val
690                 695                 700

Leu Arg Gly Asp Gly Pro Ile Ser Lys Arg Ala Ile Leu Ala Glu Glu
705                 710                 715                 720

Phe Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Val Gly Leu Thr Ser
        755                 760                 765

Trp Leu Asn Ile Lys Lys Ser
    770                 775

<210> SEQ ID NO 62
<211> LENGTH: 6
<212> TYPE: PRT
<213> ORGANISM: Artificial Sequence
<220> FEATURE:
<223> OTHER INFORMATION: synthetic peptide linker

<400> SEQUENCE: 62

Gly Thr Gly Gly Gly Gly
 1               5

<210> SEQ ID NO 63
<211> LENGTH: 6
<212> TYPE: PRT
<213> ORGANISM: Artificial Sequence
<220> FEATURE:
<223> OTHER INFORMATION: synthetic poly His, polyhistidine epitope tag,
      metal chelate affinity ligand binding moiety,
      six adjacent histidines

<400> SEQUENCE: 63

His His His His His His
 1               5